(12) United States Patent
Barker et al.

(10) Patent No.: US 8,501,434 B2
(45) Date of Patent: Aug. 6, 2013

(54) METHOD FOR PROCESSING NON-LIQUID BIOLOGICAL SAMPLES WITH DYNAMIC APPLICATION OF A PROCESSING LIQUID

(75) Inventors: Stephen Barker, Concord, CA (US); Saradha Avantsa, Concord, CA (US)

(73) Assignee: Biocare, LLC, Concord, CA (US)

( * ) Notice: Subject to any disclaimer, the term of this patent is extended or adjusted under 35 U.S.C. 154(b) by 0 days.

(21) Appl. No.: 13/463,500

(22) Filed: May 3, 2012

(65) Prior Publication Data
US 2012/0214191 A1     Aug. 23, 2012

Related U.S. Application Data

(63) Continuation of application No. PCT/US2011/055161, filed on Oct. 6, 2011.

(60) Provisional application No. 61/390,437, filed on Oct. 6, 2010.

(51) Int. Cl.
*G01N 1/30* (2006.01)
(52) U.S. Cl.
USPC ............ 435/40.5; 435/40.51; 435/40.52
(58) Field of Classification Search
None
See application file for complete search history.

(56) References Cited

U.S. PATENT DOCUMENTS

| | | | |
|---|---|---|---|
| 4,146,414 A * | 3/1979 | Stormby | 156/57 |
| 4,436,822 A | 3/1984 | Eseifan | |
| 4,569,758 A | 2/1986 | Sandulyak et al. | |
| 4,635,791 A | 1/1987 | Jackson et al. | |
| 4,949,069 A | 8/1990 | Wilson | |
| 5,023,187 A | 6/1991 | Koebler et al. | |
| 5,024,933 A | 6/1991 | Yang et al. | |
| 5,124,203 A | 6/1992 | Leatherman | |
| 5,232,664 A | 8/1993 | Krawzak et al. | |
| 5,246,665 A | 9/1993 | Tyranski et al. | |
| 5,308,460 A | 5/1994 | Mazid et al. | |
| 5,319,974 A | 6/1994 | Lenz et al. | |
| 5,344,637 A | 9/1994 | Camiener | |
| 5,425,918 A | 6/1995 | Healey et al. | |

(Continued)

FOREIGN PATENT DOCUMENTS

| | | |
|---|---|---|
| WO | 2004059287 A2 | 7/2004 |
| WO | 2005024385 A2 | 3/2005 |
| WO | 2010078176 A1 | 7/2010 |
| WO | 2012048154 A1 | 4/2012 |

OTHER PUBLICATIONS

Male, D. et al., Immunology Seventh Edition, Mosby Elsevier, 2006.

(Continued)

*Primary Examiner* — Yelena G Gakh
(74) *Attorney, Agent, or Firm* — Santangelo Law Offices, P.C.

(57) ABSTRACT

Systems and methods of sample (1) and staining processing including compression and dynamic movement of liquids (3) in a fluidically moving substantially contained liquid bridge (6) perhaps between a hydrophobic wand (4) and a hydrophilic sample support element (2). Embodiments may include low volume reagent and perhaps even low volume buffer wash in sample processing. In addition, antibodies can be conjugated with nanoparticles (64) and can be used in sample processing. Exposing a sample with or without movement to AC, DC, or even a permanent magnet field may improve staining. Staining with nanoparticle reagents could be quantified using a microscope with a magnetometer below the slide viewing area. The detection of nanoparticles attached to the chemistry may facilitate the quantification of cancerous cells stained in the tissue.

19 Claims, 16 Drawing Sheets

U.S. PATENT DOCUMENTS

| | | |
|---|---|---|
| 5,439,649 A | 8/1995 | Tseung et al. |
| 5,595,707 A | 1/1997 | Copeland et al. |
| 5,645,114 A | 7/1997 | Bogen et al. |
| 5,650,327 A | 7/1997 | Copeland et al. |
| 5,654,199 A | 8/1997 | Copeland et al. |
| 5,654,200 A | 8/1997 | Copeland et al. |
| 5,839,091 A | 11/1998 | Rhett et al. |
| 5,947,167 A | 9/1999 | Bogen et al. |
| 5,948,359 A | 9/1999 | Kalra et al. |
| 5,985,669 A | 11/1999 | Palander |
| 6,045,759 A | 4/2000 | Ford et al. |
| 6,093,574 A | 7/2000 | Druyor-Sanchez et al. |
| 6,096,271 A | 8/2000 | Bogen et al. |
| 6,183,693 B1 | 2/2001 | Bogen et al. |
| 6,192,945 B1 | 2/2001 | Ford et al. |
| 6,296,809 B1 | 10/2001 | Richards et al. |
| 6,349,264 B1 | 2/2002 | Rhett et al. |
| 6,352,861 B1 | 3/2002 | Copeland et al. |
| 6,358,473 B1 | 3/2002 | Coello et al. |
| 6,451,551 B1 | 9/2002 | Zhan et al. |
| 6,489,167 B1 | 12/2002 | Morgan et al. |
| 6,495,106 B1 | 12/2002 | Kalra et al. |
| 6,534,008 B1 | 3/2003 | Angros |
| 6,537,818 B2 | 3/2003 | Reinhardt et al. |
| 6,541,261 B1 | 4/2003 | Bogen et al. |
| 6,554,798 B1 | 4/2003 | Mann et al. |
| 6,582,921 B2 | 6/2003 | Elghanian et al. |
| 6,582,962 B1 | 6/2003 | Richards et al. |
| 6,598,474 B2 | 7/2003 | Purpura et al. |
| 6,632,598 B1 | 10/2003 | Zhang et al. |
| 6,635,225 B1 | 10/2003 | Thiem et al. |
| 6,649,368 B1 | 11/2003 | Aghassi et al. |
| 6,735,531 B2 | 5/2004 | Rhett et al. |
| 6,746,851 B1 | 6/2004 | Tseung et al. |
| 6,783,733 B2 | 8/2004 | Bogen et al. |
| 6,800,249 B2 | 10/2004 | De la Torre-Bueno |
| 6,827,901 B2 | 12/2004 | Copeland et al. |
| 6,855,292 B2 | 2/2005 | Angros |
| 6,855,552 B2 | 2/2005 | Towne et al. |
| 6,855,559 B1 | 2/2005 | Christensen et al. |
| 6,866,881 B2 | 3/2005 | Prentice et al. |
| 6,903,207 B2 | 6/2005 | Mirkin et al. |
| 6,943,029 B2 | 9/2005 | Copeland et al. |
| 6,998,270 B2 | 2/2006 | Tseung et al. |
| 7,025,937 B2 | 4/2006 | Plank |
| 7,067,325 B2 | 6/2006 | Christensen et al. |
| 7,070,951 B2 | 7/2006 | Zhang et al. |
| 7,074,175 B2 | 7/2006 | Handy et al. |
| 7,115,386 B2 | 10/2006 | Posthuma |
| 7,118,918 B2 | 10/2006 | Copeland et al. |
| 7,198,752 B2 | 4/2007 | Thiem |
| 7,217,392 B2 | 5/2007 | Bogen et al. |
| 7,226,788 B2 | 6/2007 | De La Torre-Bueno |
| 7,250,301 B2 | 7/2007 | Angros |
| 7,287,388 B2 | 10/2007 | Dorenkamp et al. |
| 7,300,452 B2 | 11/2007 | Gleich |
| 7,303,725 B2 | 12/2007 | Reinhardt et al. |
| 7,303,729 B2 | 12/2007 | Plank |
| 7,318,913 B2 | 1/2008 | Loeffler et al. |
| 7,351,194 B2 | 4/2008 | Gleich |
| 7,359,536 B2 | 4/2008 | Hays et al. |
| 7,400,983 B2 | 7/2008 | Feingold et al. |
| 7,410,753 B2 | 8/2008 | Hopkins et al. |
| 7,435,383 B2 | 10/2008 | Tseung et al. |
| 7,468,161 B2 | 12/2008 | Reinhardt et al. |
| 7,470,541 B2 | 12/2008 | Copeland et al. |
| 7,476,362 B2 | 1/2009 | Angros |
| 7,481,980 B2 | 1/2009 | Gausepohl |
| 7,494,823 B2 | 2/2009 | Sukumar |
| 7,510,555 B2 | 3/2009 | Kanzius |
| 7,550,298 B2 | 6/2009 | Towne et al. |
| 7,553,672 B2 | 6/2009 | Bogen et al. |
| 7,584,019 B2 | 9/2009 | Feingold et al. |
| 7,585,964 B2 | 9/2009 | Palanisamy et al. |
| 7,593,787 B2 | 9/2009 | Feingold et al. |
| 7,603,201 B2 | 10/2009 | Feingold et al. |
| 7,615,371 B2 | 11/2009 | Kram |
| 7,618,807 B2 | 11/2009 | Lemme et al. |
| 7,622,077 B2 | 11/2009 | Angros |
| 7,627,381 B2 | 12/2009 | Kanzius et al. |
| 7,632,461 B2 | 12/2009 | Angros |
| 7,648,678 B2 | 1/2010 | Favuzzi et al. |
| 7,718,435 B1 | 5/2010 | Bogen et al. |
| 7,722,811 B2 | 5/2010 | Konrad et al. |
| 7,744,817 B2 | 6/2010 | Bui |
| 7,758,809 B2 | 7/2010 | Favuzzi et al. |
| 7,820,381 B2 | 10/2010 | Lemme et al. |
| 7,838,283 B2 | 11/2010 | Erickson et al. |
| 7,850,912 B2 | 12/2010 | Favuzzi et al. |
| 7,867,443 B2 | 1/2011 | Key et al. |
| 7,875,242 B2 | 1/2011 | Shah |
| 7,875,245 B2 | 1/2011 | Favuzzi et al. |
| 7,897,106 B2 | 3/2011 | Angros et al. |
| 7,901,941 B2 | 3/2011 | Tseung et al. |
| 7,935,534 B2 | 5/2011 | Lemme et al. |
| 7,937,228 B2 | 5/2011 | Feingold et al. |
| 7,951,612 B2 | 5/2011 | Angros et al. |
| 7,960,178 B2 | 6/2011 | Key et al. |
| 2002/0072122 A1 | 6/2002 | Copeland et al. |
| 2003/0092029 A1 | 5/2003 | Josephson et al. |
| 2003/0124729 A1 | 7/2003 | Christensen et al. |
| 2003/0175852 A1 | 9/2003 | Kalra et al. |
| 2004/0009098 A1 | 1/2004 | Torre-Bueno |
| 2004/0033163 A1 | 2/2004 | Tseung et al. |
| 2004/0058328 A1 | 3/2004 | Chan et al. |
| 2004/0266015 A1 | 12/2004 | Favuzzi et al. |
| 2005/0074890 A1 | 4/2005 | Lemme et al. |
| 2005/0164374 A1 | 7/2005 | Kram |
| 2006/0019302 A1 | 1/2006 | Lemme et al. |
| 2006/0088928 A1 | 4/2006 | Sweet et al. |
| 2006/0134793 A1 | 6/2006 | Key et al. |
| 2006/0148063 A1 | 7/2006 | Fauzzi et al. |
| 2006/0153436 A1 | 7/2006 | Haras |
| 2006/0246524 A1 | 11/2006 | Bauer et al. |
| 2006/0265133 A1 | 11/2006 | Cocks et al. |
| 2006/0281116 A1 | 12/2006 | Angros et al. |
| 2007/0048770 A1 | 3/2007 | Jaekel et al. |
| 2007/0196909 A1 | 8/2007 | Showalter et al. |
| 2007/0231889 A1 | 10/2007 | Angros |
| 2008/0038836 A1 | 2/2008 | Reinhardt et al. |
| 2008/0102006 A1 | 5/2008 | Kram et al. |
| 2008/0176769 A1 | 7/2008 | Rank et al. |
| 2008/0194034 A1 | 8/2008 | Erickson et al. |
| 2008/0213804 A1 | 9/2008 | Erickson et al. |
| 2008/0318305 A1 | 12/2008 | Angros |
| 2009/0004691 A1 | 1/2009 | Erickson et al. |
| 2009/0029392 A1 | 1/2009 | Josephson et al. |
| 2009/0069335 A1 | 3/2009 | Ji et al. |
| 2009/0090855 A1 | 4/2009 | Kobold et al. |
| 2009/0181398 A1 | 7/2009 | Bauer et al. |
| 2009/0258362 A1 | 10/2009 | Brees et al. |
| 2010/0003189 A1 | 1/2010 | Tlsty et al. |
| 2010/0009429 A1 | 1/2010 | Angros |
| 2010/0028978 A1 | 2/2010 | Angros |
| 2010/0068096 A1 | 3/2010 | Angros |
| 2010/0068102 A1 | 3/2010 | Angros |
| 2010/0164489 A1 | 7/2010 | Lukaszew et al. |
| 2011/0150725 A1 | 6/2011 | Angros et al. |
| 2011/0151504 A1 | 6/2011 | Avantsa et al. |

OTHER PUBLICATIONS

Wilson, J. et al., Molecular Biology of the Cell, Fourth Edition, Garland Science, 2002.

Aveyard, R., et al. Capillary condensation of vapours between two solid surfaces: effects of line tension and surface forces; Surfactant Science Group, Department of Chemistry, University of Hull, Hull UK; Phys. Chem. Chem. Phys, 1999, 1, 155-163.

Bouaidat, S. et al. Surface-directed capillary sytsem; theory, experiments and applicants; The Royal Society of Chemistry 2005, Lap Chip, 2005, 5, 827-836.

Finn, R. Capillary Surface Interfaces, Notices of the AMS; vol. 46, No. 7, pp. 770-781, Aug. 1999.

Bhushan, B. et al., Adhesion and stiction: Mechanisms, measurement techniques, and methods for reduction; J. Vac. Sol. Technol. B 21(6). Nov./Dec. 2003.

Wang, L, et al. Capillary Forces between Submillimeter Spheres and Flat Surfaces at Constant Liquid Volumes; Chin. Phys. Lett. vol. 26, No. 12 (2009).

Montero, C. The Antigen-Antibody Reaction in Immunohistochemistry; the Journal of Histochemistry & Cytochemistry; vol. 51(1); 1-4, 2003.

Hiratsuka, K. et al. Water droplet lubrication between hydrophilic and hydrophobic surfaces; 1OP Science; 2007 J. Phys.: Conf. Ser. 89 (2007) 012012;.

Potteli, K. K. Cancer Detection using Nanoparticles; ECG653 Project Report; Fall 2008.

Perez-Madrid, a. et al., Brownian Motion in the Presence of a Temperature Gradient, arXiv:cond-mat19505137v1, submitted on May 26, 1995.

Aculon SAMP Technology for Best in Class Surface Treatments, 2 Pages.

Hocking, L.M. et al.; The Spreading of a Drop by Capillary Action, J. Fluid Mech. (1982) vol. 121, pp. 425-442.

Fowler, Michael; "Viscosity, Introduction: Friction at the Moledular Level", Uva. 6126/2007, 15 Pages.

Brenner, Howard., "Brownian motion in the presence of temperature gradiants: an extension of Einstein's theory on the 100th anniversary of its formulation," Dept. of Chem. Engineering, MIT.

Saravanan, J.B. et al.; "Molecular dynamics simulations of nanocrop motion on uniform and non-uniform surfaces," Clarkson University, Dept. of Chem. Engineering and Center for Advanced Materials Processing.

U.S. Appl. No. 61/390,437, filed Oct. 6, 2010, entitled Immunohistochemistry Staining Process by Moving Reagent on Slide Using Hydrophobic Wand.

International Application No. PCT/2011/055161, International Search Report dated Feb. 14, 2012.

International Application No. PCT/2011/055161, Written Opinion of the International Searching Authority dated Feb. 14, 2012.

* cited by examiner

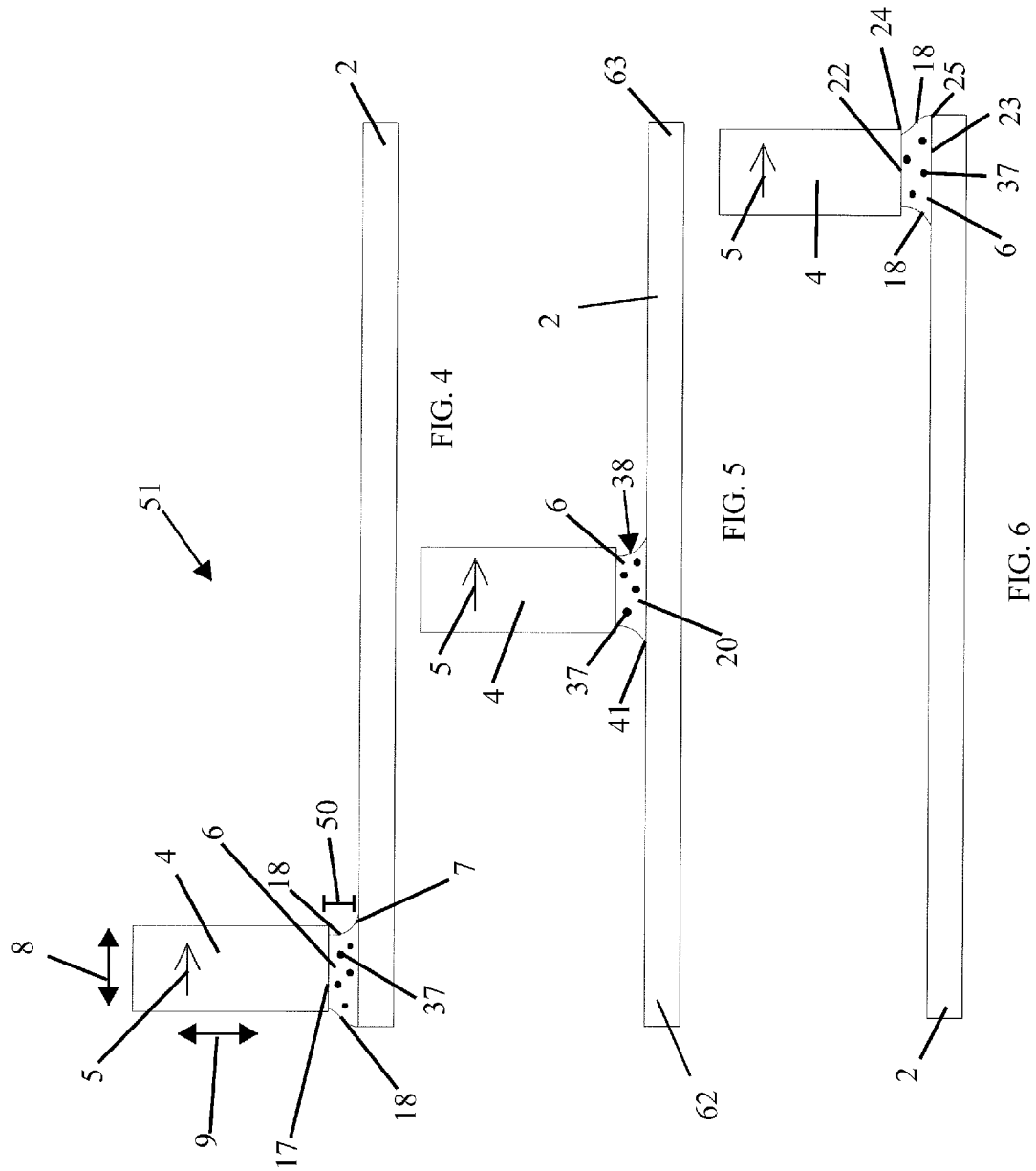

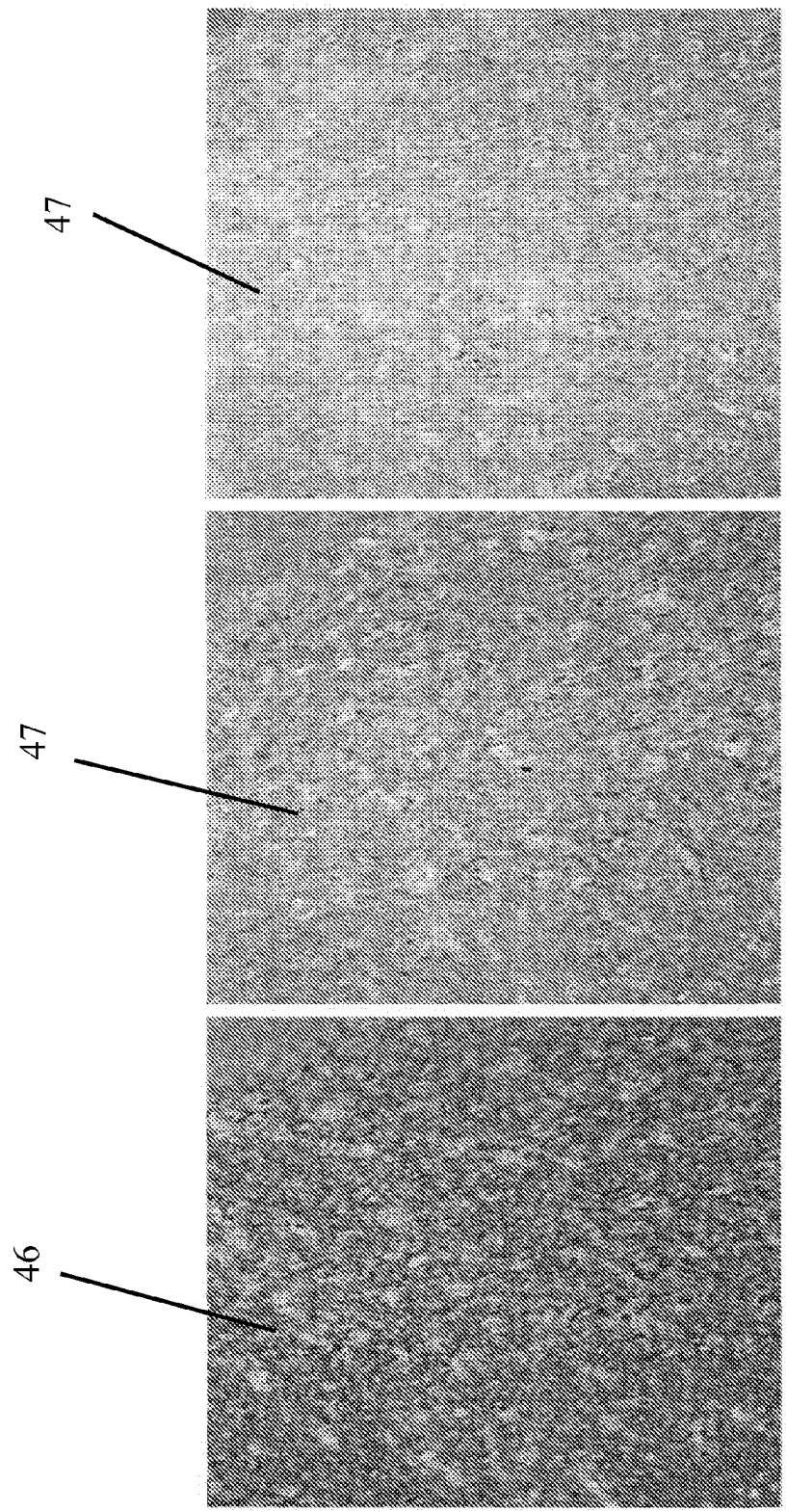

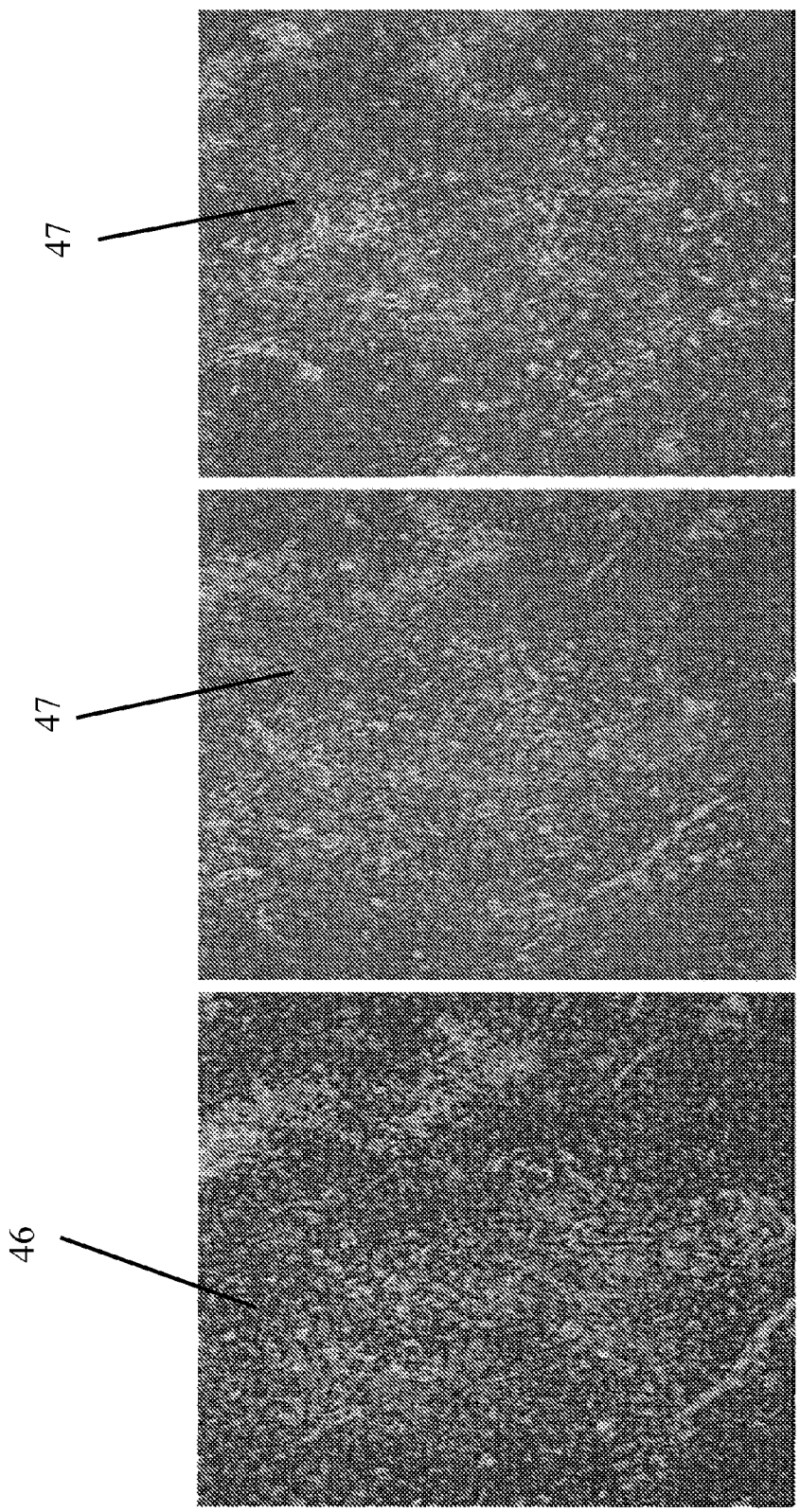

US 8,501,434 B2

METHOD FOR PROCESSING NON-LIQUID BIOLOGICAL SAMPLES WITH DYNAMIC APPLICATION OF A PROCESSING LIQUID

CROSS-REFERENCES TO RELATED APPLICATIONS

This application is a continuation of International Patent Application Number PCT/US2011/055161, filed Oct. 6, 2011 which claims the benefit of and priority to U.S. Provisional Application No. 61/390,437 filed Oct. 6, 2010, each hereby incorporated by reference herein in their entirety.

TECHNICAL FIELD

The present invention is directed to the field of immunohistochemistry and in-situ hybridization staining processes on primarily, but not limited to, formalin fixed paraffin embedded tissue samples using various reagents to include antibodies, DNA/RNA probes of interest and perhaps even various buffer solutions where in the process, liquids may be moved in a controlled manner across the surface of a sample and slide. Embodiments of the present invention may include staining processes by perhaps moving a reagent on a tissue perhaps held between a hydrophobic surface and a hydrophilic surface with an antigen retrieved and/or deparaffinized tissue sample. The present invention may relate to automated immunohistochemistry tissue staining processing systems and methods of processing samples and staining. The present invention may be applicable to immunohistochemistry, in-situ hybridization, fluorescent in-situ hybridization, special staining, such as special staining of histological samples, microarray sample processing, cytology, as well as potentially other chemical and biological applications.

BACKGROUND OF THE INVENTION

Sample processing in chemical and biologic analyses, such as immunohistochemical (IHC) applications, may require one or a number of various processing sequences, steps, and/or protocols as part of an analysis of one or more samples. The staining sequences, steps and/or protocols may be defined by the individual or organization requesting an analysis, such as a pathologist or histologist of a hospital, and may be further defined by the particular analysis to be performed.

Previously, in some traditional processing sequences, protocol steps may have been performed manually, potentially creating a time-intensive protocol and necessitating personnel to be actively involved in the sample processing. Attempts have been previously made to automate sample processing to address the need for expedient sample processing and a less manually burdensome operation. However, such previous efforts may not have fully addressed the needs for an efficient sample processing system in that they may not provide excellent staining results with perhaps with little or no background or non specific staining. Embodiments of the present invention may address the failures of previous attempts by providing stainer methods and systems with a shorter completion time, may significantly reduce the process time. Embodiments of the present invention may provide methods and systems where a liquid such as a reagent may be moved across a slide in a controlled manner and may produce crisp, sharp staining with perhaps little or no background, no non-specific staining in the tissue, and perhaps even no hue on the glass slide.

Past efforts at automated sample processing for samples presented on carriers such as slides, such as U.S. Pat. No. 7,820,381 to Lemme et al., U.S. Pat. No. 7,615,371 to Kram, US Publication No. US2005/0074890 to Lemme et al., U.S. Pat. No. 5,985,669 to Palander, US Publication No. US2008/1012006A1 to Kram et al., U.S. Pat. No. 6,352,861 to Copeland et al., and U.S. Pat. No. 5,839,091 to Rhett et al., each hereby incorporated by reference herein, have not afforded the various advantages and other combinations of features as presented herein. The systems of the prior art do not provide the efficient processing with excellent staining results like that of the present invention.

DISCLOSURE OF THE INVENTION

The present invention discloses methods and systems for sample processing and efficient staining systems which may address the inadequacies of previous stainer and sample processing technology. It is an object of the present invention to establish an oscillating liquid movement over a sample to perhaps generate efficient and even excellent staining results of the sample.

It is another object of the present invention to apply electrical or magnetic fields while processing a sample.

It is yet another object of the present invention to generate an oscillating liquid movement over a sample with an oscillating wand such as a hydrophobic wand which may hold and oscillate the liquid over the sample and may even provide optimal contact angles between the wand, the moving liquid, and the sample supported by a sample support element for optimal processing.

Another object of the present invention may provide an oscillating liquid bridge movably held between a hydrophobic wand and a hydrophilic sample support element for sample processing.

It is still another object of the present invention to provide efficient use of liquids in a sample processing system. Embodiments include providing low volume reagent use with sample processing. Other embodiments provide that less or even no wash steps may be needed to clean a sample and slide and the wash steps may need only a low volume of buffer to clean the slides.

It is yet another object of the present invention to provide nanoparticles in a liquid during a sample processing system which may be used in the evaluation of the sample or may even be used to enhance activity of the liquid with the sample during processing.

Naturally, further objects of the invention are disclosed throughout other areas of the specification and claims.

BRIEF DESCRIPTION OF THE DRAWINGS

The accompanying figures illustrate some of the embodiments of the present invention, and together with the written disclosures of the specification and claims, facilitate an understanding of the disclosed embodiments.

FIG. 4 shows an example of a side view of a liquid bridge held in between a wand and a sample support element as the wand and liquid bridge begins to move across the sample support element from an end point in accordance with some embodiments of the present invention.

FIG. 5 shows an example of a side view of a liquid bridge held in between a wand and a sample support element as the wand and liquid bridge continues to move across a middle of a sample support element in accordance with some embodiments of the present invention.

FIG. 6 shows an example of a side view of a liquid bridge held in between a wand and a sample support element as the wand and liquid bridge moves to the other end point of a sample support element in accordance with some embodiments of the present invention.

FIG. 20 shows an example of the staining results of CD10 on Tonsil, cell membrane staining with an oscillating hydrophobic wand and oscillating liquid bridge over a sample supported by a sample support element.

FIG. 21 shows an example of the staining results of CD10 on Tonsil, cell membrane staining from a conventional stainer for a convention amount of processing time.

FIG. 22 shows another example of the staining results of CD10 on Tonsil, cell membrane staining from a conventional stainer for a less amount of processing time.

FIG. 23 shows an example of the staining results of Cyclin D1 on Mantle cell lymphoma—nuclear staining with an oscillating hydrophobic wand and oscillating liquid bridge over a sample supported by a sample support element.

FIG. 24 shows an example of the staining results of Cyclin D1 on Mantle cell lymphoma—nuclear staining from a conventional stainer for a conventional amount of processing time.

FIG. 25 shows another example of the staining results of Cyclin D1 on Mantle cell lymphoma—nuclear staining from a conventional stainer for a less amount of processing time.

MODES FOR CARRYING OUT THE INVENTION

Figure 1:
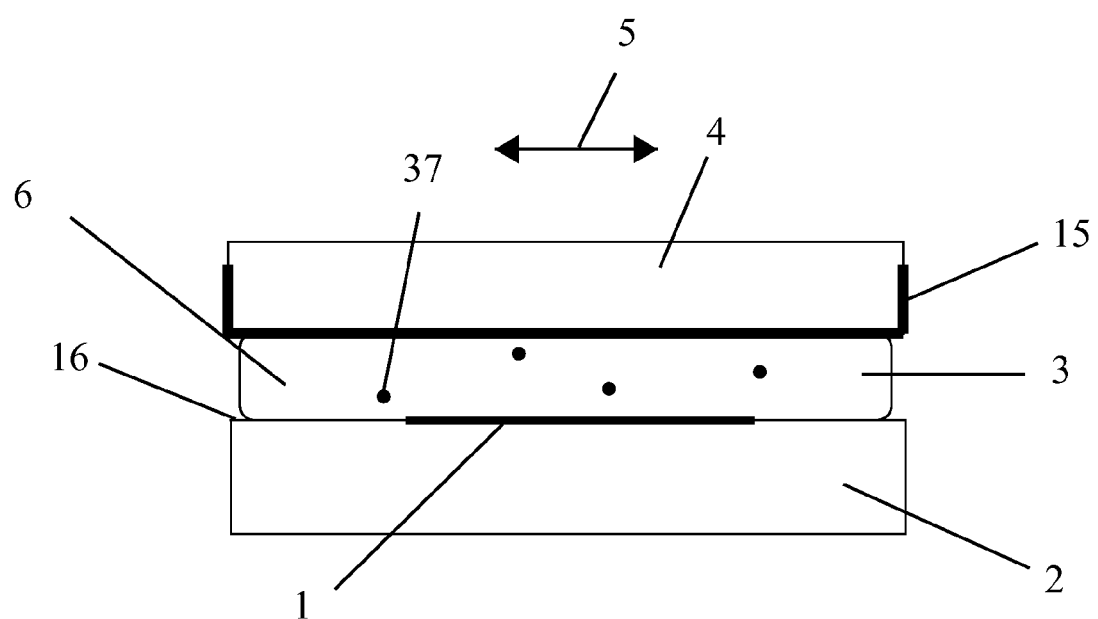
FIG. 1 is an example of a wand with hydrophobic coating holding a liquid between the wand and the tissue and sample support element in accordance with some embodiments of the present invention.

The present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should be understood to support and encompass descriptions and claims of all the various embodiments, systems, techniques, methods, devices, and applications with any number of the disclosed elements, with each element alone, and also with any and all various permutations and combinations of all elements in this or any subsequent application.

Aspects of the present invention may be applicable to immunohistochemistry, in-situ hybridization, fluorescent in-situ hybridization, special staining of histological samples, micro arrays, including techniques incorporating deparaffinization, target retrieval, staining of samples, formalin fixed paraffin embedded ("FFPE") tissue, any other samples, and the like. Sample processing applications may require processing sequences or protocols that include steps such as deparaffinization, heat induced antigen or epitope retrieval, staining, immunohistochemistry techniques, in-situ hybridization techniques, or the like. Stains such as histochemical reagents may be used to identify various histological features. The reagents used in a stain process may employ antibodies that bind to specific proteins of the sample. In regards to staining, it should be understood that the term stained sample can reference the end product of a process, by which certain parts of the sample may be stained, e.g., have been imbued with a reagent that adheres to a specific element in the tissue. The adhered reagent may be with a color in the optic range or even in an electromagnetic range, such as ultra violet. Staining may be detectable with a stain detection of a stain result which may include but is not limited to automatic detection, change in property detection, fluorescent detection, magnetic detection, electrical detection, visual detection, radioactive detection, calorimetric detection, and qualitative detection, or the like. Staining a sample can involve a series of treatment steps, such as but not limited to washing, binding of reagents to the specific parts of the sample, activation of the reagents, washing unbound antibodies, detection of the antibody, any combination thereof, and the like. Sample processing with the reagents may require the addition and removal of reagents in accordance with a defined protocol.

Immunohistochemistry ("IHC") applications may be a multiple step staining process where perhaps different reagents may be dispensed on a sample and/or sample support element. Immunohistochemistry may be an in-vitro (perhaps not in-vivo) staining performed on formalin fixed paraffin embedded ("FFPE") tissue. IHC may be performed in a sequence of steps, including but not limited to: (1) a tissue may be exposed to deparaffinization perhaps followed by heat induced epitope retrieval and/or enzyme digestion; (2) application of a primary antibody may be applied to attach to a target epitope of interest, this may be at least about 30 minutes (the binding of an antibody to an epitope can be accelerated by selected favorable conditions that may affect the kinetics of the binding reaction); (3) application of a secondary antibody may be applied to attach to a primary antibody, this may be between about 10 and about 30 minutes; (4) application of a tertiary antibody may be applied to attach to a secondary antibody; this may be between about 10 and about 30 minutes; (5) application of a chromogenic substrate compatible (i.e. reactive) with the antibody-enzyme conjugate may be applied; this may be between about 5 and about 20 minutes. The reaction of the enzyme and substrate may produce a visible chromogenic product that can be visualized under a microscope perhaps as a qualitative test.

Embodiments of the present invention may provide methods and systems for efficient processing of samples where a liquid may be dynamically applied to a sample during the processing. As understood from FIG. 1, a sample (1) may be supported by a sample support element (2). A wand (4) may be located above a sample and sample support element and may even be an oscillating wand so that the wand may be oscillated back and forth above the sample to create an oscillating wand movement (5). A liquid (3) may be applied to the sample (1) and even the sample support element (2) and may form a fluidically moving substantially contained liquid bridge (6) between a wand (4) and a sample supported by a sample support element (2). A fluidically moving substantially contained liquid bridge may be contained and even oscillated with the movement of the wand movement to provide back and forth movements over a sample. The movement of the fluidically moving substantially contained liquid bridge over a sample may provide a dynamic contact of the fluidically moving substantially contained liquid bridge with the sample.

In embodiments, a wand (4) may be a steadily controlled oscillating wand providing steady oscillations back and forth above a sample. A wand movement (5) may be a steady oscillation wand movement and may horizontally oscillates in a horizontal movement (8) above a sample support element perhaps even without substantially any vertical movement (9) of the wand as shown in FIG. 4. As such, a wand may oscillate in a fashion that it cannot substantially move up or down, e.g., vertically, above the sample. Alternatively, a wand may move in a vertical movement in other embodiments.

Figure 3:
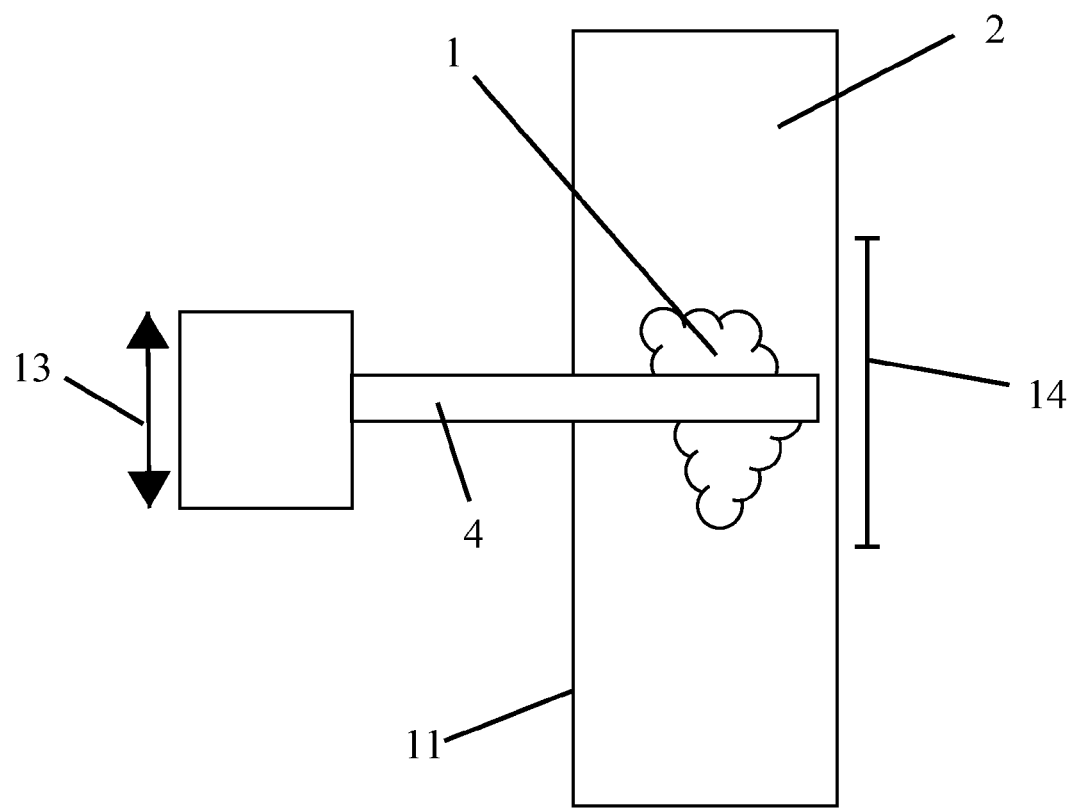
FIG. 3 is an example of a wand placed for movement along a length of a sample support element in accordance with some embodiments of the present invention.
Figure 7:
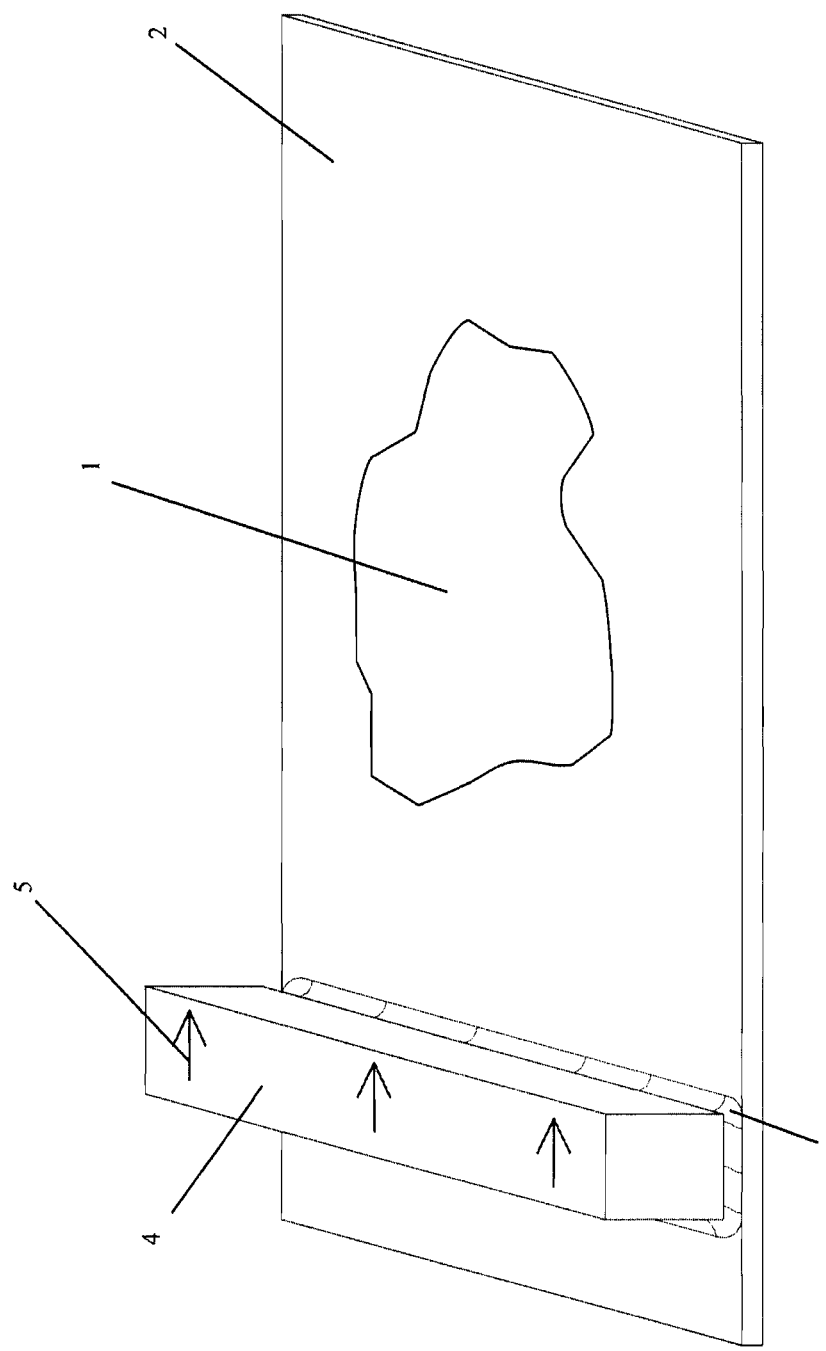
FIG. 7 shows an example of top perspective view of movement of a wand with a liquid bridge across a sample and a sample support element starting at an end point of a sample support element in accordance with some embodiments of the present invention.
Figure 8:
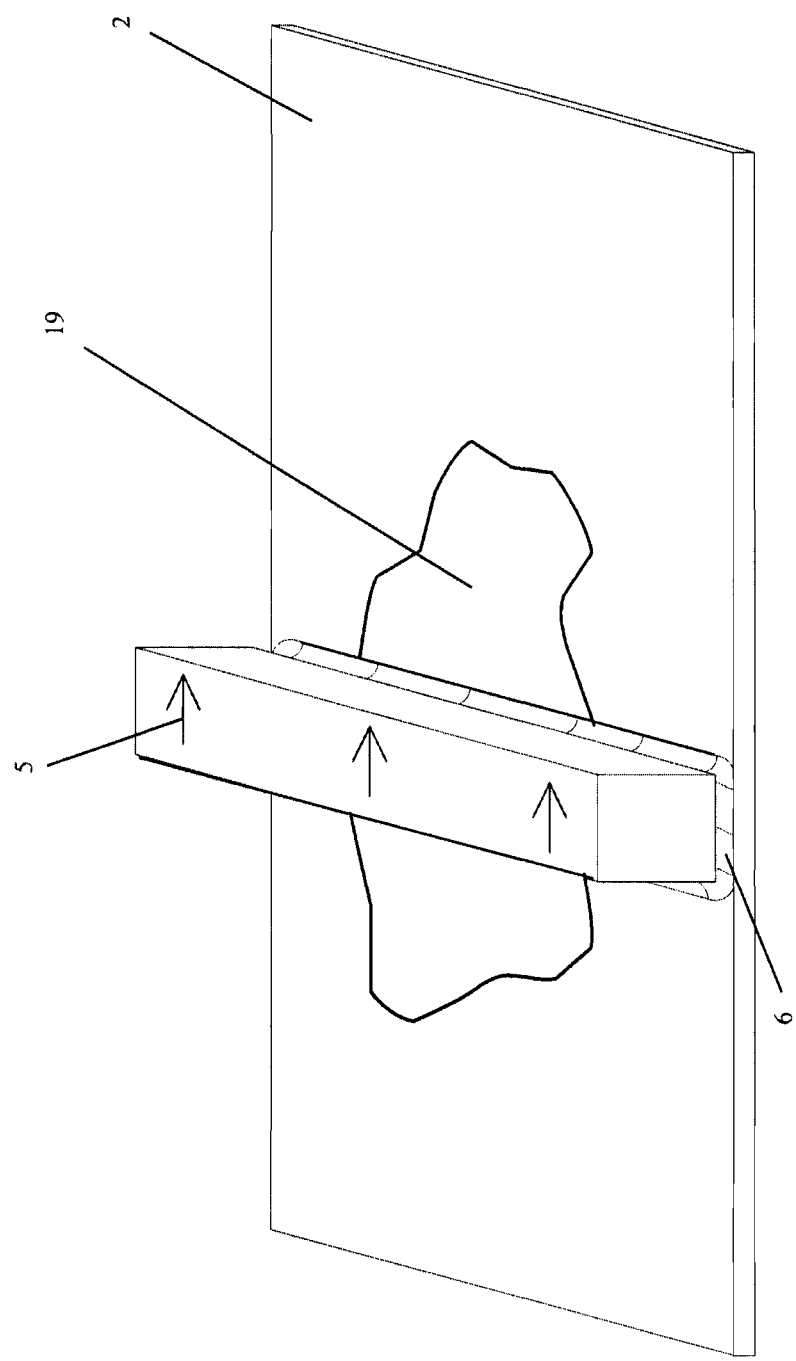
FIG. 8 shows an example of top perspective view of movement of a wand with a liquid bridge across a sample and a sample support element across a middle of the sample support element in accordance with some embodiments of the present invention.
Figure 9:
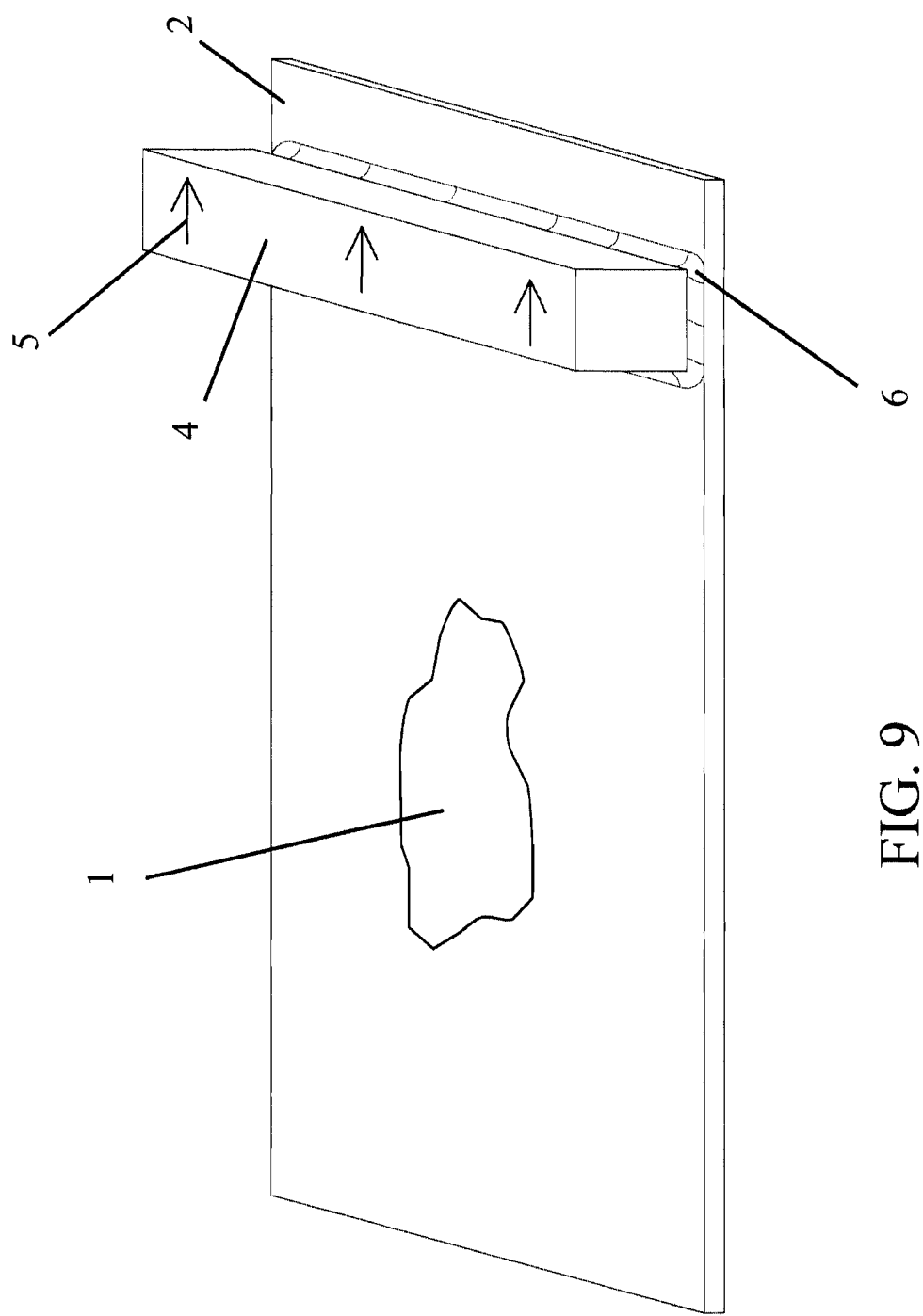
FIG. 9 shows an example of top perspective view of movement of a wand with a liquid bridge across a sample and a sample support element ending at the other end point of a sample support element in accordance with some embodiments of the present invention.

A wand (4) may be an inflexible wand where it may not be bent or adaptable and may be rigid. A wand (4) may be floating wand so that it may be located above the sample and even the sample support element without having any contact or even direct contact with the sample or the sample support element. A wand (4) may be a non-gas permeable wand such that gas or even liquid may not be capable of permeating or even penetrating the wand. A wand (4) may be any shape, figure, material, form, or even size including but not limited to rectangle, curve, substantially flat, slender, stick, rod, shoot, or the like. A wand (4) may partially cover a sample as shown in the example of FIG. 3 or alternatively, a wand may fully cover a sample as shown in FIG. 1. In both instances, a wand may be oscillated so that a fluidically moving substantially contained liquid bridge may be oscillated with it and the liquid bridge may either partially cover the sample or alternatively fully cover the sample.

A substantially flat wand (17) may be a wand which has a wand surface in contact with a liquid that may be substantially flat perhaps lying horizontal to a sample support surface at its full length. A wand (4) may be oscillated above a sample in a variety of wand movements (5) such as but not limited to a continuously moving wand which may continuously move back and forth above a sample; a uniformly moving wand which may uniformly move back and forth above a sample; a steady velocity moving wand which may steady velocity move back and forth above a sample, a variable velocity moving wand which may variable velocity move back and forth above a sample, or the like. The various wand movements may be achieved by a system (49) connected to a wand which may include but is not limited to a manual system for perhaps manually oscillating of a wand, an automated system for perhaps automatically oscillating of a wand, a robotic system for perhaps robotically oscillating of a wand, an electromechanical system, a computerized system, or the like.

Figure 2:
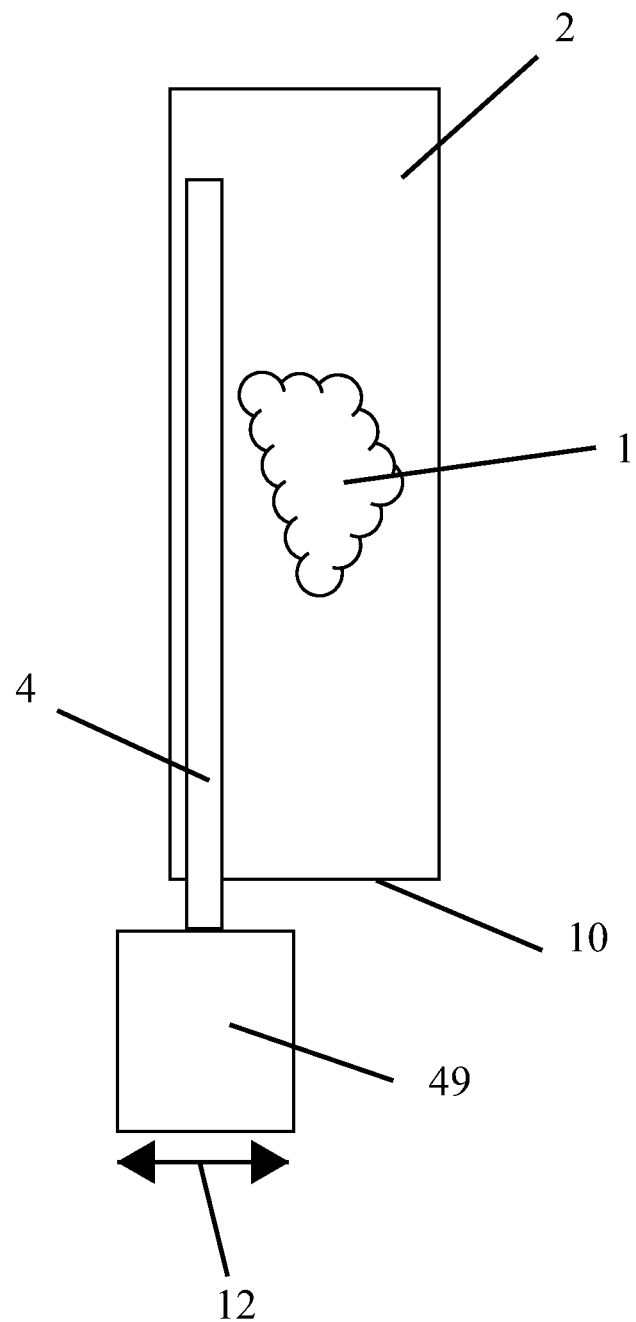
FIG. 2 is an example of a wand placed for movement along a width of a sample support element in accordance with some embodiments of the present invention.

As can be understood from FIGS. 4, 5 and 6 and FIGS. 7, 8 and 9, a wand (4) with a liquid formed into a fluidically moving substantially contained liquid bridge (6) may move across a sample on a sample support element perhaps from one end (62) of a sample support element to the other end (63) of the sample support element and may continue oscillating back and forth between the ends. As the wand moves, it may collect and may hold substantially all of the volume of liquid into a substantially contained liquid bridge (6) between the wand and the sample support element. Of course, some of the liquid, perhaps even very small amounts of the liquid may be removed from the liquid bridge and may remain with the sample as staining, attraction, or the like may occur. In embodiments, a wand (4) with the substantially contained liquid bridge could move (12) along the width (10) of a sample support element as shown in FIG. 2, could move (13) along the length (11) of a sample support element (2) as shown in FIG. 3, could move across a sample support element in a diagonal fashion, could move across a sample so that each movement distance (14) may cover all of a sample (1) as shown in FIG. 3, could move in any combination of the above, or the like. In embodiments, a wand (4) may be oscillated back and forth with the substantially contained liquid bridge above a sample for a programmed incubation time. This may include a reagent stain time, a buffer wash time, a primary antibody stain time, a secondary antibody stain time, a tertiary antibody stain time, or the like.

A wand (4) may be placed at a distance above a sample and/or sample support element providing a gap (50). While any distance for a gap may be used, the distance may be calculated so that liquid contained in a substantially contained liquid bridge may be optimally contained therein. If the gap between the wand and the sample and/or sample support element is too wide, the liquid bridge may not remain intact and liquid may spread and may even lay flat as a thin layer on the sample or sample support element surface. If the gap is too small, the liquid in the liquid bridge may be too compressed so that the liquid bridge may not have optimal performance.

In one embodiment, a gap may be a size between about 0.5 mm and about 0.6 mm. A cohesive force of a liquid sandwiched between a wand perhaps even a hydrophobic wand and a sample and/or sample support element, perhaps even a hydrophilic sample support element, in a gap may allow the liquid bridge to stay intact.

In embodiments, it may be desirable to provide a wand (4) that is a hydrophobic wand. A hydrophobic wand may be any type of wand that has little or no affinity for water and/or liquids. A hydrophobic wand may any kind of hydrophobic surface element and may be made of a hydrophobic material or may even have a hydrophobic surface (15) such as coated with a hydrophobic coating. A hydrophobic surface may be a nanostructured hydrophobic surface, a nanostructured rough hydrophobic surface, or perhaps even a coating of self-assembled monolayer of phosphates, or the like. In embodiments, a sample support element (2) may be a hydrophilic sample support element which may have a hydrophilic surface (16). A hydrophilic surface on the slide may be important for an immunohistochemistry staining process. During the reagent application steps, the hydrophilic (e.g., wettable) slide surface properties may allow for uniform distribution of reagents across an entire slide surface perhaps resulting in an evenly stained slide.

A fluidically moving substantially contained liquid bridge (6) may be located in a gap between a bottom surface of a wand and a top surface of a sample and/or sample support element. As the fluidically moving substantially contained liquid bridge may move along a sample with a wand movement, the liquid bridge may be in dynamic contact (7) with a sample. Dynamic contact may be fluid action, fluid motion, energy related, force related, changing contact, electrical, magnetic, or the like. Due to the interactions of a fluidically moving substantially contained liquid bridge (6) with a sample and/or sample support element, a processing protocol may be used perhaps with less wash steps or even without any wash steps during the process. A fluidically moving substantially contained liquid bridge using to staining a sample may itself wash the sample and/or sample support element perhaps providing an efficient system with less steps needed.

Figure 10:
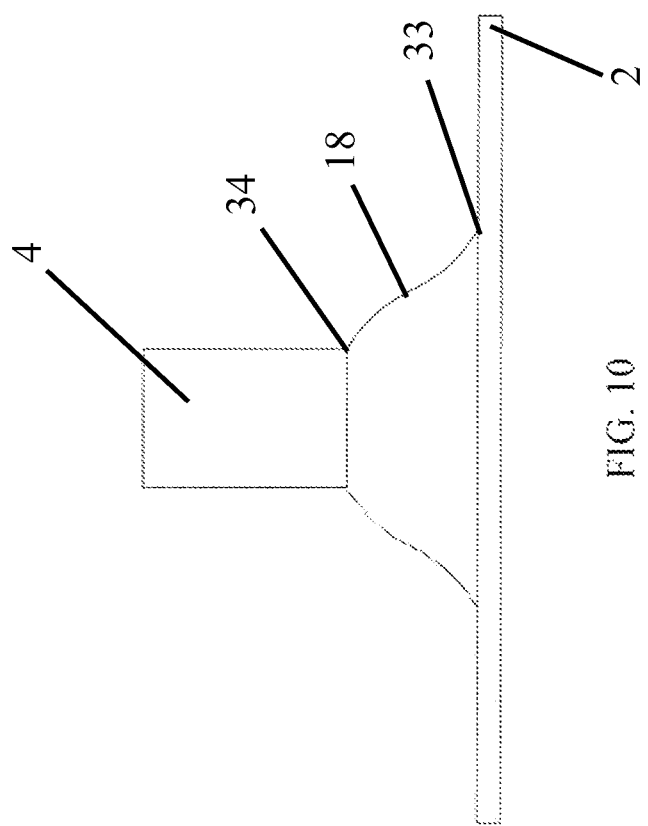
FIG. 10 shows an example of a meniscus and contact angles of a liquid bridge between a wand and a sample support element in accordance with some embodiments of the present invention.
Figure 11:
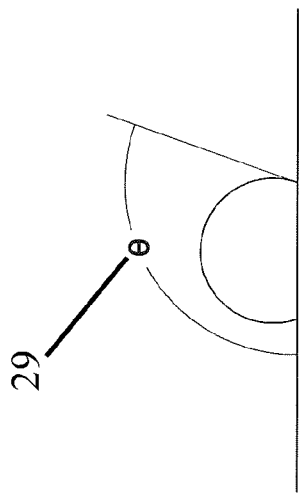
FIG. 11 shows an example of a hydrophilic contact angle in accordance with some embodiments of the present invention.
Figure 12:
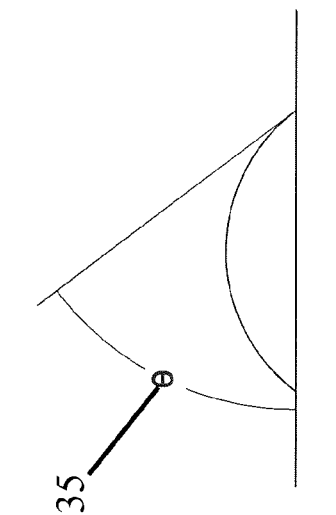
FIG. 12 shows an example of a hydrophobic contact angle in accordance with some embodiments of the present invention.

A fluidically moving substantially contained liquid bridge may provide a contact angle with the surface of a wand (22) and a contact angle with a surface of a sample and/or sample support element (23). In embodiments, the present invention may provide acutely contacting a liquid bridge with a sample support element at an acute liquid to sample support element contact angle (25). In addition or perhaps even alternatively, the present invention may provide obtusely contacting a liquid bridge with a wand at an obtuse liquid to wand contact angle (24). A meniscus (18) as shown in FIG. 10 may form a meniscus surface curve between the contact angles at each end of the liquid bridge. Each end of a meniscus surface curve may be different and it may fluidically change as the liquid bridge moves and oscillates with the wand movement along the sample and sample support element. A meniscus surface curve may move based on the physical movement of the wand and perhaps even the liquid bridge. However, the contact angles at the wand and at the sample and sample support surfaces may remain substantially the same as the wand and liquid bridge oscillate back and forth over the sample. This may be dependent on the type of wand and sample support element used such as a hydrophobic wand and a hydrophilic sample support element as discussed herein. The acute liquid to sample support element contact angle (25) may be a dynamic contact angle perhaps due to its fluidic movement along with sample support element. The obtuse liquid to wand contact angle (24) may be a dynamic contact angle perhaps due to its fluidic movement within the liquid bridge as the bridge and wand oscillate over the sample and sample support element. As conceptually shown in FIG. 11, an acute liquid to sample support element contact angle may be a decreased contact angle (35) and may be an angle that is less than 90 degrees. As conceptually shown in FIG. 12, an obtuse liquid to wand contact angle may be an increased contact angle (29) and may be greater than 90 degrees. A contact angle may be a quantitative measure of the wetting of a solid by a liquid. It may be defined geometrically as an angle formed by a liquid at the three phase boundary where a liquid, gas, and solid intersect. Low values of contact angles may indicate that a liquid may spreads or may even wets well while a high value for a contact angle may indicate poor wetting. If an angle is less than 90 degrees, a liquid may wet a solid. If an angle is greater than 90 degrees, it may be non-wetting.

Embodiments of the present invention may provide a hydrophilic sample support element perhaps with a hydrophilic surface and may even provide a hydrophobic wand with perhaps a hydrophobic surface. Embodiments of the present invention may provide that as roughness on a sample support element may increase, an acute liquid to sample support element contact angle may decrease. The interaction of a hydrophilic surface with a liquid may provide an adhesive force between the fluidically moving substantially contained liquid bridge and the sample support element that is greater than a cohesive force within a fluidically moving substantially contained liquid bridge. These interactions may form the acute contact angle. The interaction of a hydrophobic wand with a liquid may provide a cohesive force within a fluidically moving substantially contained liquid bridge that is greater than an adhesive force between the fluidically moving substantially contained liquid bridge and the wand. These interactions may form the obtuse contact angle. When placing a liquid between a hydrophilic sample support surface and a hydrophobic wand surface, the interactions may provide an optimal substantially contained liquid bridge for use with sample processing.

Figure 13:
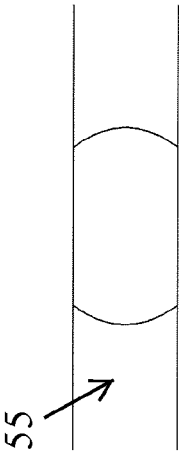
FIG. 13 shows an example of a liquid contact between a hydrophilic top surface and a hydrophilic bottom surface in accordance with some embodiments of the present invention.
Figure 14:
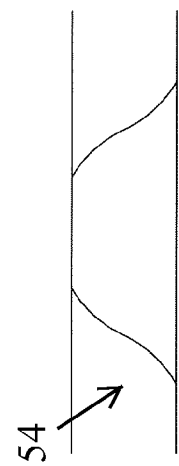
FIG. 14 shows an example of a liquid contact between a hydrophobic top surface and a hydrophilic bottom surface in accordance with some embodiments of the present invention.
Figure 15:
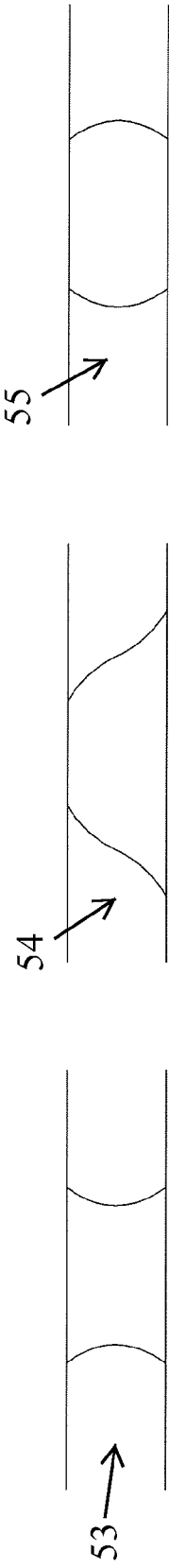
FIG. 15 shows an example of a liquid contact between a hydrophobic top surface and a hydrophobic bottom surface in accordance with some embodiments of the present invention.

The contact angles and meniscus surface curve may be understood from FIGS. 11, 12, 13, 14, and 15. When two hydrophilic surfaces (53), such as a hydrophilic wand surface with a hydrophilic sample support element, may be provided to form a liquid bridge, a meniscus surface curve between the hydrophilic surfaces may have concave properties perhaps due to the decreased contact angles and interactions with the liquid as shown in FIG. 13. When two hydrophobic surfaces (55), such as a hydrophobic wand with a hydrophobic sample support element, may be provided to form a liquid bridge, a meniscus surface curve between the hydrophobic surfaces may have convex properties perhaps due to the increased contact angles and interactions with the liquid as shown in FIG. 15. The different contact angles and meniscus surface curve between a top hydrophobic surface and a bottom hydrophilic surface (54) is shown in FIG. 14. Embodiments of the present invention provide that a sample may be optimally treated when using a hydrophobic wand and a hydrophilic sample support element and oscillating a liquid bridge between these surfaces and in contact with a sample.

A liquid bridge may be compressed between a wand and sample wherein surface tension holding of a liquid and liquid bridge may be provided. For example, as the liquid such as a reagent may move, it may be compressed and friction force (e.g., sliding reagent friction) may be produced perhaps in combination with mixing. This may be a factor for achieving an equilibrium constant of antigen antibodies binding faster to perhaps reduce incubation time and reaction time. The total volume of reagent may be held by the wand and as the wand may move at a steady velocity, the mass of reagent, perhaps held by surface tension or even by weak, non-covalent interactions, may move with the wand. Surface tension may be the result of the tendency of water molecules to attract one another (e.g., cohesion). Many IHC reagents may be mixed with Tween 20 (less than about 1%) and perhaps other surfactants which may reduce the surface tension of water based reagents and may aid in better spreading. A sample support surface may be in a solid state and the surface of the slide may have a thin layer of wash buffer and perhaps even a target tissue/epitope to make it hydrophilic. As a liquid bridge of reagent may move, the reagent may wet the tissue instantaneously perhaps due to hydrophilic attraction. A bridge of reagent may be sandwiched between the hydrophobic wand and the hydrophilic glass slide surface.

As discussed, a meniscus (18) may be formed at each end of the fluidically moving substantially contained liquid bridge. As the fluidically moving substantially contained liquid bridge may move along a sample (1) it may provide an instantaneous wetting (19) of the sample surface with the liquid perhaps due to the dynamic contact between the sample and the liquid. Due to the oscillating movement of the liquid bridge, the sample may be continuously wetted as the liquid bridge moves back and forth over the sample. The oscillating movement may also provide a sliding friction (20) between the liquid bridge and a sample.

The movement of reagent may increase the reaction rate and perhaps a reaction or incubation time may be decreased perhaps due to several factors including but not limited to: intermolecular forces, capillarity, angle of contact (meniscus), wetting or wet ability, kinetic energy, sliding friction of reagent, Brownian motion, capillary painting, capillary sliding of reagent, capillary drag, surface tension, adhesive and/or cohesive force and factors, Van der Waal forces, electrostatic force, capillary bridge, liquid bridge, reagent bridge, reagent painting, pH, concentration of antibody, buffer constituents, salts added, dilution used, temperature, buffer to render the electrostatic charges of the epitope or paratope identical, or the like. The staining may be completed in less than 30 or about 45 minutes or perhaps even up to about 1 hour including deparaffinization and retrieval time as compared to a minimal of about 2 hours in staining process of conventional automated stainers.

A reaction rate may be accelerated and to achieve equilibrium, for example by: 1) increasing the rate of forming favorable antibody-epitope interactions or perhaps even 2) increasing the rate of breaking up unfavorable antibody-epitope interactions or even removal of poorly matched or poorly bound or removal of non-specific binding. As the liquid such as a reagent may be moved across the slide, redistribution of antibodies to the target tissue may be achieved by mixing the reagent in-between the slide with hydrophilic attraction and may facilitate the binding of antibody to epitope in the tissue perhaps due to movement of reagent.

A sample may be any material including but not limited to a biological sample, biological material, tissue, specimen, antigen retrieved tissue, epitope retrieved tissue, deparaffinized tissue, histological sample, cells, cell specimens, cell lines, proteins, cell membrane, synthetic peptides, cell preparations, blood, bodily fluids, bone marrow, cytology specimens, blood smears, thin-layer preparations, micro array sample, microscopic slide-based biological samples, formalin fixed paraffin embedded tissue samples, preserved sample, any combination thereof, or the like. In preparation for biologic sample analysis, for example, a biological sample may be acquired by known sample acquisition techniques and may comprise, for example in immunohistochemistry (IHC) applications, tissues generally or even in some applications one or a plurality of isolated cells, such as in micro array samples, and may be presented on a sample carrier such as a microscope slide. Furthermore, the sample may be presented on the carrier variously and potentially in some form of preservation. As one example, a sample such as a layer or slice of tissue may be preserved in formaldehyde and presented on a carrier with one or more paraffin or other chemical layers infiltrating the sample.

In embodiments, a sample support element (2) may include but is not limited to a sample carrier, a slide, a glass slide, a microscope slide, a thin glass plate, a smooth surface member, and the like. A sample support element (2) may be tilted to provide a tilted sample support element during part or even the entire staining process sequence. For example, a sample support element may be tilted at an angle between about 3 and about 45 degrees. Of course, during the processing of a slide, a sample support element may be placed in any position or angle such as but not limited to a substantially flat position, a horizontal position, a vertical position, an interchangeable position, a substantially flat position during oscillating of a fluidically moving substantially contained liquid bridge, a stationary position, and a moveable position and may even change between different positions. The liquid bridge may move with the wand perhaps and may stay within the slide area even with tilt or angle and the liquid may not cross the area of wand.

A liquid (3) as discussed herein may be any kind of fluid that may be desirable for a sample processing protocol or system. A liquid (3) may include but is not limited to at least one reagent, at least one water based reagent, at least one unstable reagent, at least one stable reagent, at least one buffer solution, at least one immunohistochemistry reagent, at least one in situ hybridization reagent, at least one histochemical reagent, any combination thereof, or the like. Reagents can play a vital role in the staining sequence of many processing protocols. The quality of the reagents, therefore, may be important for adequate sample processing. Reagents, for example, can have a certain shelf life that may be limited if maintained at undesirable temperatures such as the typical ambient temperatures of traditional processing systems and the laboratories housing such systems. Traditional technologies may lack the temperature control needed to optimally preserve the reagents stored in the processing system that are often subject to inadequate or changing ambient temperatures of such systems and the laboratory environment.

An isolated cold station may be included in an automated stainer, in embodiments of the present invention, to perhaps maintain a temperature from between about 2° C. and about 8° C. to maintain the stability of unstable reagents. Liquids including unstable reagents or even stable reagents perhaps with one or a plurality of components may be mixed onboard before application of a mixed reagent onto a slide. Alternatively, the liquid perhaps with at least one component (37) or even at least two components may be on-slide mixed. For example, liquids such as unstable reagents or stable reagents and perhaps even one or more than one component (37) may be dispensed on a slide and a hydrophobic wand may collect the reagent forming a liquid bridge and may move the reagent as discussed herein and as may be understood from FIGS. 4, 5 and 6. A hydrophobic wand may be a mixing wand to perform on-slide or even online mixing. A liquid perhaps with components therein may be on-slide mixed (38) due to movement of the liquid bridge and may be used for staining a sample. The mixing (38) of a liquid and at least one component within an oscillating fluidically moving substantially contained liquid bridge across a sample and sample support element may provide redistribution of the components perhaps as a component redistributor to a sample or may even provide uniform application of the components to a sample perhaps as a uniform applicator. For example, a reagent moving with a wand may allow redistribution or mixing of antibodies which may result in uniform concentration of antibodies across a slide.

A component may include but is not limited to an antibody, a DNA probe, a RNA probe, a particle, a nanoparticle, a micro particle, a salt, a primary antibody, a secondary antibody, a tertiary antibody, a chromogenic substrate, a counterstain compatible with an antibody-enzyme conjugate, a surfactant, a component capable of reducing surface tension of a water based reagent, any combination thereof, and the like.

In accomplishing a processing sequence, and in some embodiments of the present invention, slides may be configurable in vertical, horizontal or perhaps even tilted positions such as for the pretreatment and/or staining processes. This may allow for the automation of the pretreatment and staining of slides in various manners. The slides may be initially loaded onto carrier retention assemblies, such as slide racks, and drawers in perhaps the horizontal position. The slides may be horizontally supported by adjustable carrier supports. If pretreatment is required, such as deparaffinization, the slide tray or holder or carrier may be tilted at an angle and the antigen retrieval solution may be maintained at a desired temperature to complete the antigen retrieval process. Cold water may be pumped in to an inside chamber to perhaps cool the inside chamber to an ambient temperature such as about 25° C.+/−(between about 2 to about 4° C.). To perform a staining process on the slides, as described herein and in some embodiments, a system may rotate the slide to the horizontal position and a syringe or probe or reagent dispense may apply fluid to the sample, providing a horizontal staining of the sample. Each slide or plurality of slides can be rotated independently allowing for the independent processing of different samples with different requirements.

A slide station may be arranged inside an automated stainer perhaps in a slide carrier or tray or even a carousal with the capability of slides positioned lying flat or even tilted at an angle. One slide or even a plurality of slides may be held in support using slide clips or perhaps even support mechanisms to hold the slide during staining process. A drive or even a motor can be used to move the slides and reagents during staining process.

As discussed herein, processing of a sample may be automated and may occur via various steps or protocols based on the desired application. Sample processing may comprise one or more sampling protocols and steps, such as deparaffinization, target retrieval, staining, or the like. A tissue may be washed with a buffer between reagent applications. Reagents, buffers, and incubation times may vary based on the type of assay.

Embodiments may provide a sample processing system where a sample may be pretreated with a sample pretreatment element (39) perhaps prior to staining of the sample. A sample pretreatment element (39) may include a process such as but not limited to deparaffinization, antigen retrieval, epitope retrieval, heat induced antigen retrieval, antigen retrieval, epitope retrieval, proteolytic-induced epitope retrieval, any combination thereof, and the like which may include a processor element such as but not limited to deparaffinization element, antigen retrieval element, epitope retrieval element, heat induced antigen retrieval element, antigen retrieval element, epitope retrieval element, proteolytic-induced epitope retrieval, any combination thereof, and the like.

Protocol for treatment of a sample may be processed in accordance with immunohistochemistry, in-situ hybridization, fluorescent in-situ hybridization, special staining, special staining of histological samples, microarray sample processing, cytology, automated processing of any of the above, any combination thereof, and the like. A processed sample (43) may result after a sample may be treated with any of the various protocols or systems. Embodiments of the present invention may provide a staining of a sample with perhaps a decreased reaction time which may be about half an amount of time as compared to a standard stain time.

Figure 19:
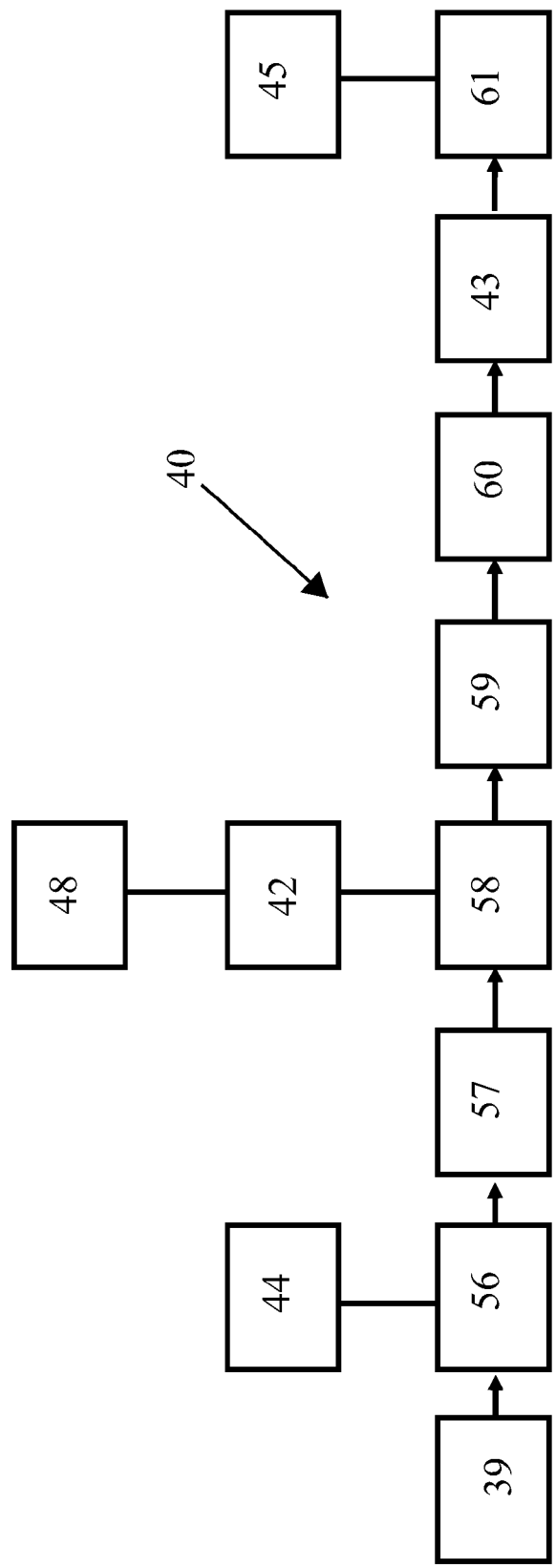
FIG. 19 is a flow chart diagram showing an example of a sample processing protocol in accordance with some embodiments of the present invention.
Figure 28:
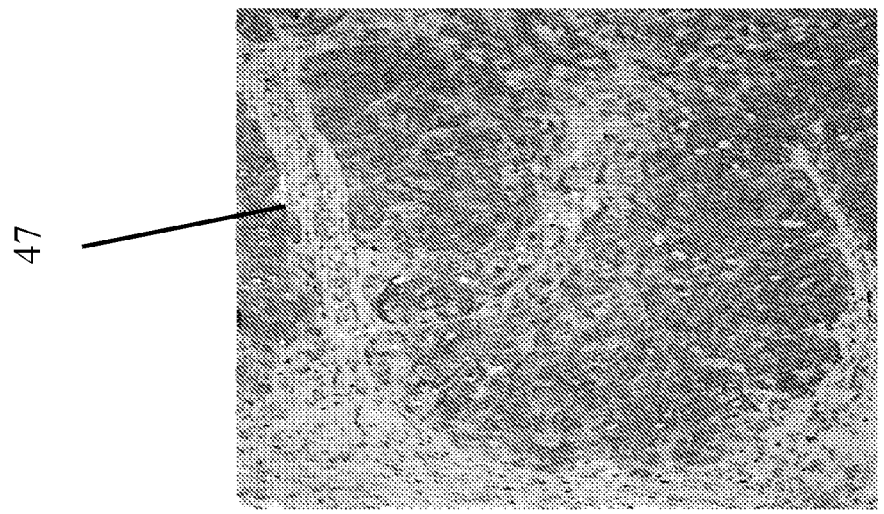
FIG. 28 shows another example of the staining results of Pan melanoma on Melanoma—Cytoplasmic staining from a conventional stainer for a less amount of processing time.
Figure 27:
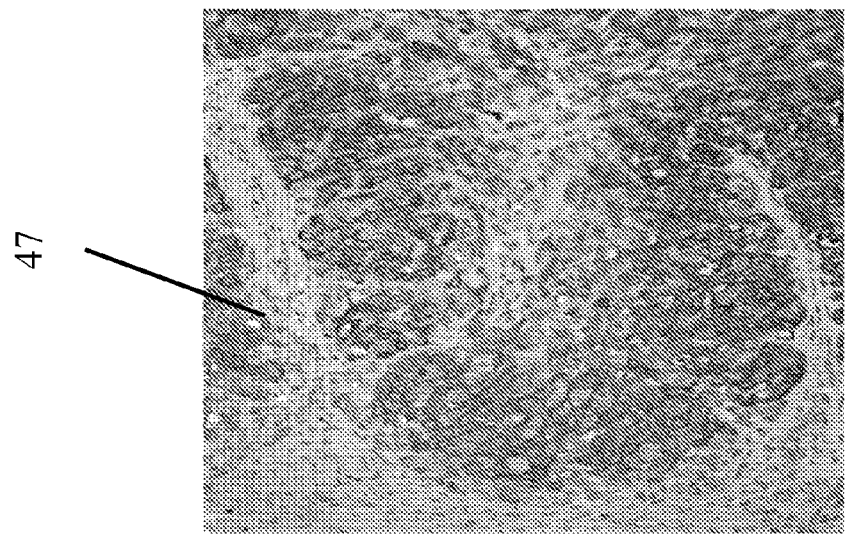
FIG. 27 shows an example of the staining results of Pan melanoma on Melanoma—Cytoplasmic staining from a conventional stainer for a conventional amount of processing time.

FIG. 19 provides a non-limiting example of a processing steps (40) as may be used for processing of a sample which may be a manual process or even an automated process. First, a sample may be pretreated (39). Then, then a liquid such as a reagent may be applied (56) to a sample perhaps supported by a sample support element perhaps for staining of the sample with the liquid. A liquid temperature controller (44) may regulate a temperature of a liquid. An activity enhancer (57) may be applied to the liquid on a sample to perhaps increase staining performance which may include any of a variety of enhancement techniques such as but not limited to creating an oscillating fluidically moving substantially contained liquid bridge between a hydrophobic wand and a hydrophilic sample support element; applying a magnetic or electrical field to a liquid which may or may not have nanoparticles therein; or the like as discussed herein. A sample may then be washed (58) with a buffer wash. The buffer wash or any liquid on a sample may be removed with a removal element (42) and waste may be collected from a sample and/or sample support element with a waste collector (48). A waste collector (48) may separate the waste into hazardous waste and non-hazardous waste. A second liquid such as a reagent may be applied (59) to a sample perhaps for staining of the sample with the liquid. This second liquid application step may also include an activity enhancer if desired. A second wash step (60) may then occur. After the sample has been stained, a processed sample (43) may be provided. The processed sample (43) may be a stained sample and it may be analyzed (61) with perhaps an evaluation element (45). Evaluation (45) of a processed sample may include but is not limited to stain detection, magnetic detection, magnetic microscope detection and the like as discussed herein. Of course, the steps discussed in this example of a process protocol may be skipped or varied depending on the desired sample protocol. In embodiments, a protocol sample processing may occur in an open air system (51) perhaps providing that some or even all of the processes and steps may be processed to the open air and not closed.

Figure 26:
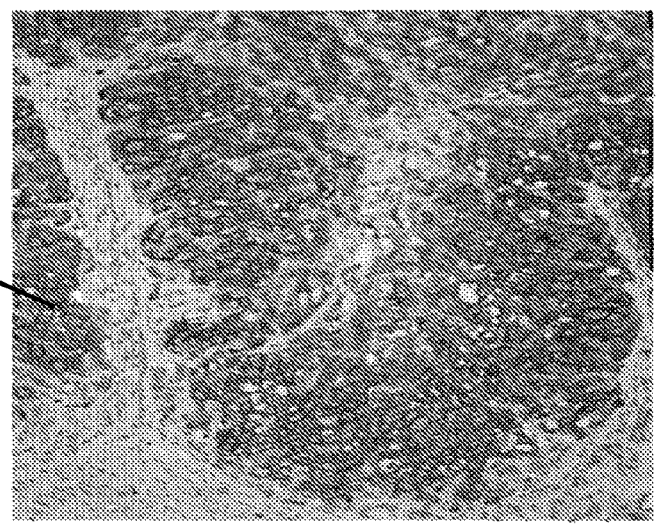
FIG. 26 shows an example of the staining results of Pan melanoma on Melanoma—Cytoplasmic staining with an oscillating hydrophobic wand and oscillating liquid bridge over a sample supported by a sample support element.

A stained sample may have a property including but not limited to a sharp stain (46), a crisp stain, a stained sample with substantially no background, a stained sample with substantially no non-specific staining, a stained sample with substantially no hue on the sample support element, or the like. Examples of stained samples using an oscillating hydrophobic wand and oscillating fluidically moving substantially contained liquid bridge technology are shown in FIGS. 20, 23, and 26. Examples of results from conventional staining (47) with an IQ technology are shown in FIGS. 21, 22, 24, 25, 27, and 28. It is surprising to see the differences in results between the convention technologies and the present invention. It is noted that FIGS. 20, 22, 23, 25, 26, and 28 were stained at a shorter reaction time (e.g., 15-5-5-2) as compared to FIGS. 21, 24, and 27 (e.g., 30-10-10-5).

Figure 18:
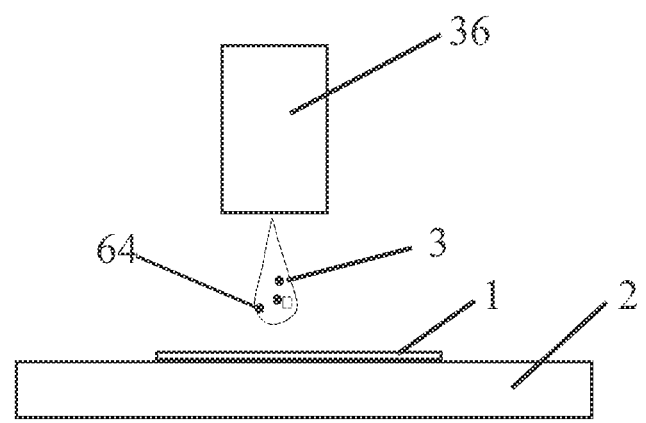
FIG. 18 shows an example of a liquid applicator applying liquid to a sample supported by a sample support element in accordance with some embodiments of the present invention.

The present invention may provide in embodiments, sample processing with a low volume of liquid. For example, an automated stainer may be a low volume processor perhaps using very minimal liquid such as reagent per slide as compared to conventional automated stainers which may use between about 250 to about 300 microliters per slide or even up to about 1000 micro liters per reagent step. As shown in FIG. 18, a liquid applicator (36) may apply a low volume of liquid (3) to a sample (1) supported by a sample support element (2). A liquid applicator may be any kind of liquid dispensing element including but not limited to manual, automatic, robotic arm, and the like which may be capable of applying a low volume of liquid to a sample. A reagent dispensing operation may be dispensed from a reagent bottle and a principle may be based on bird feeder gravity flow with perhaps precise volume delivery. A low volume liquid process may provide that a liquid may be used at as low as between about 15 microliters and about 300 microliters perhaps for in-situ hybridization protocol, between about 50 microliters and about 300 microliters, about 100 microliters, about 150 microliters, less than about 150 microliters, and the like. Of course any amount of liquid may be used in a sample processing system perhaps even up to about 1000 micro liters per reagent step. However, it may be desirable to provide a system that may use less liquid so as to provide efficiencies in costs, waste, time, processing, and the like.

A low volume liquid process may be applied to a system or may even be a result of a system where the low volume liquid may be held in an oscillating fluidically moving substantially contained liquid bridge perhaps even between a hydrophobic wand and a hydrophilic glass slide surface. A low volume liquid may include a reagent with perhaps even at least one component or even at least two components as discussed herein. A dynamic contact of the liquid bridge formed from a low volume amount with a sample may provide efficient staining, or perhaps even cleaning of a sample supported by a sample support element.

The present invention may provide, in embodiments, sample processing with low volume liquid washing of a sample with a low volume of buffer wash. A liquid applicator (36) may apply a low volume of liquid (3) such as buffer wash to a sample (1) supported by a sample support element (2). The volume of buffer used to wash per step may also be very low compared to conventional automated stainers. The typical volume of buffer used with air knife and/or air blow methods of removal of buffer may be between about 10 milliliters and about 15 milliliters of buffer. In embodiments, a low volume buffer wash may include an amount of buffer less than about 1 milliliter, between about 500 microliters and about 1 milliliter (1000 microliters), up to about 10 milliliters, between about 5 milliliters and about 6 milliliters of buffer per step, slide wash, wash step or the like. In embodiments, liquid from a low volume buffer may be moved across a sample and sample support element in an oscillating fluidically moving substantially contained liquid bridge perhaps even between a hydrophobic wand and a glass slide with a sample. A dynamic contact of the liquid bridge formed from a low volume amount with a sample may provide efficient staining, or perhaps even cleaning of a sample supported by a sample support element. A moving buffer in a liquid bridge (6) and a trailing edge (41) of meniscus with perhaps the right volume of reagent and wash buffer may clean a slide better and may even produce a slide with no hue and/or no background on the tissue perhaps with crisp staining. A trailing edge (41) of a wash buffer meniscus of a fluidically moving substantially contained liquid bridge may be a sample cleaner and may electrostatically attract at least some impurities on a sample and sample support element and may clean the slide with perhaps less buffer solution.

A buffer wash may be a warm buffer wash perhaps at a temperature of between about 25° C. and about 40° C. or even at about 37° C. may be used to clean the sample support element and may aid in better cleanliness for hue on a glass slide and may even provide little to no background on a tissue. In embodiments, a sample or slide may not be heated but the buffer may heated to between about 25° C. and about 40° C. perhaps using an inline heater just before dispensing on the slide. An inline heating concept may be employed for on slide antigen retrieval process and antigen retrieval solution and may be dispensed at between about 30° C. to about 98° C. A separate dispensing line can be used for the buffer dispensing or as the volume per run may be as low as about 5 to about 6 mls per slide, a bottle with ready to use buffer can be used for dispensing warm buffer.

Embodiments of the present invention may provide removal of a buffer wash or perhaps any liquid on a sample and/or sample support element with a liquid removal element (42) such as a buffer wash removal element. A liquid removal element (42) may include but is not limited to a vacuum, vacuum comb, wicking element, drying element or the like. A liquid removal element (42) can be used to remove the buffer from the slide which may be in a flat or even at an angled position after a reagent incubation time and perhaps before the next reagent in the step may be applied. Unbound excess reagent can be removed and buffer may be used to clean a slide which can be removed by a vacuum comb. In embodiments, a vacuum comb may remove a buffer from a bottom end of the slide. A software scheduler and perhaps protocol may determine which reagent needs to be dispensed for a particular slide after removal of a previously applied reagent. A software scheduler may apply the next regent as quickly as possible perhaps within between about 5 and about 20 seconds after removal of the excess buffer. The reagent or bulk fluid or antigen retrieval application step may be scheduled as such slides may not dry during the staining process.

Figure 16:
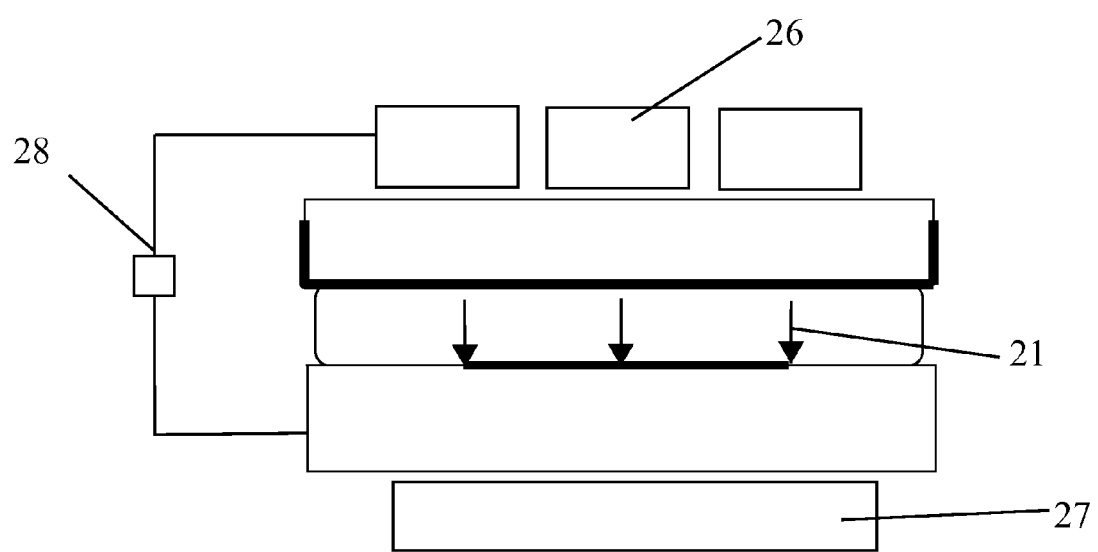
FIG. 16 shows a conceptual example of an electric field or a magnetic field applied to a liquid in a wand system in accordance with some embodiments of the present invention.

In embodiments, the present invention may provide an electrical field or a magnetic field applied to a liquid in a sample processing system. As shown in FIG. 16, an electrical field or magnetic field (21) or both or even an electromagnetic field may be applied to a liquid (3) in between a wand (4) and a sample support element (2). A field may include an AC field or a DC field and may even be varied with a field strength modifier as applied to a sample. Oscillation of a wand and a fluidically moving substantially liquid bridge may be used together with the electrical field or magnetic field. In other embodiments, electrical or magnetic fields may be applied to a sample without using wand technology as may be understood from FIG. 17. In yet other embodiments, an electrical field or a magnetic field may be moved across a sample perhaps by field movement or even by sample movement or both. A wand (4) may be a hydrophobic wand or even a conducting hydrophobic wand. A field generator (26) may be provided near a liquid and perhaps even near a wand which may include but is not limited to a conducting plate, a conducting needle, a conducting surface, multiple conducting elements, an electromagnet, a permanent magnet, and the like. A conducting plate (27) or other type of field generator may be located near or even under a sample support element. A voltage (28) may be applied between a wand and a sample support element or at a point of contact including but not limited to static voltage, variable negative voltage, DC bias voltage, DC voltage, AC voltage and the like. It may be desirable to regulate the temperature perhaps with a temperature regulator of the sample and even liquid with a liquid temperature controller during the sample processing system.

This may include providing a liquid, sample, or other system environments with a cooler, a heater, a liquid temperature between about 2° C. and about 8° C., and a liquid temperature between about 25° C. and about 100° C.

An applied electrical field or even magnetic field may increase an electrostatic charge of the reagents perhaps reducing the reaction time and even improving the quality of tissue staining. An electrostatic mechanism may allow the chemistry in a liquid to attach to a tissue receptor perhaps even in conjunction with complimentary receptor geometry. Increasing this "charge" may decrease reaction time could and staining fidelity may improve. Charge may be understood by electrostatic lines per unit area. Subjecting the lines to a transverse magnetic field in motion electronically, perhaps by reversing the polarity and even physically moving the lines by slide or even pole piece movement, new electric field lines may be generated perhaps orthogonal to the magnet field lines, and may add to the net charge in the atomic structure of the reagent. The effect may be velocity dependant and improvements may be shown with velocity and frequency increase.

Embodiments of the present invention may provide increasing the electrostatic charge of a reagent to perhaps reduce reaction time and even improving the quality of sample staining. Electrostatic force may be increased by a number of field lines in a molecular structure of a reagent. Magnetic field lines may be held constant per unit area. A reagent may be inserted within a cross section of a field. Transverse motion between a reagent and magnetic field lines may increase electrical field lines in a reagent. A magnetic field may be changed in amplitude or even polarity perhaps while holding electrostatic field lines stationary in a reagent. Utilization of all forms of changing magnetic fields perhaps by physical movement or even electronically changing field line strength may increase reagent electrical charge. Audio, white noise, periodic waves, or even ultrasonic transducer may be used.

An applied electrical field or magnetic field may vary or even change a contact angle (24) between a liquid and a surface of a wand (22) or even a contact angle (25) between a liquid and a surface of a sample support element (23). In embodiments, the electrical field or magnetic field applied to a liquid may increase a contact angle (24) between a liquid and a surface of a hydrophobic wand (22).

In embodiments, the present invention may provide a method and system of processing a sample where a liquid (3) such as a reagent may include nanoparticles (64) or even micro particles as may be understood from FIG. 18. The reagent and nanoparticles may be applied to a sample and may result in a stained sample. The stain sample may be evaluated with an evaluation element (45) such as a sample evaluation element or even a nanoparticle evaluation element. The nanoparticles (64) in the reagent may be suspended colloidal inert particles in the reagent. The nanoparticles (64) may be conjugated with an antibody to form a nanoparticle-antibody conjugate. The conjugates may then tag at least some cells in a sample when as the antibodies stain the sample. Processing of a sample with nanoparticles may occur in accordance with immunohistochemistry protocol or perhaps any other sample processing protocol.

Nanoparticles (64) may include but are not limited to magnetic nanoparticles, metal oxide nanoparticles, magnetic metal oxide nanoparticles, superparamagnetic metal oxide nanoparticles, gold nanoparticles, magnetic iron oxide nanoparticles, cadmium selenide nanoparticles, any combination thereof, and the like. Nanoparticles may be sized in the range of between about 10 nm to about 500 nm, between about 10 nm and 100 nm, or any size perhaps used in the processing of immunohistochemistry staining with nanoparticles attached to antibodies and detection. While any amount of nanoparticles may be included in a reagent, one example may be to provide about 1% of nanoparticles in a reagent for processing.

As discussed above, a stained sample may be evaluated perhaps after staining with reagent and nanoparticles. An evaluation element (45) may include but is not limited to a magnetic evaluation element; a magnetic nanoparticle evaluation element for magnetically evaluation of the nanoparticles as stained on the sample; a magnetic attraction for magnetically attracting the nanoparticles for sample analysis; a magnetic microscope; a magnetic detection for magnetically detection of nanoparticles with said sample; a magnetometer; a magnetometer combined with an image analysis system; an image analysis system; a camera; or the like. For example, staining with nanoparticle reagents could be quantified using a microscope with a magnetometer below the slide stage viewing area. A magnetometer in addition to image analysis system and perhaps even a camera may aid in locating cells with nanoparticles to quantify the staining. The detection of nanoparticles attached to the chemistry may facilitate the quantification of cancerous cells stained in the tissue.

In embodiments of the present invention, a liquid, such as a reagent, may have enhanced activity within the liquid to perhaps create efficient and even better staining of a sample. Specifically, enhancing activity of a liquid may occur through enhancing activity of nanoparticles or even micro particles contained in a reagent perhaps with a nanoparticle activity enhancement. For example, embodiments of the present invention may provide reagents with antibodies mixed with nanoparticles or even micro particles and applied for staining of samples perhaps even mounted on a sample support element such as a microscope slide. Enhancement of the activity in a liquid may include applying a magnetic field to the liquid having nanoparticles or micro particles therein. A magnetic field may excite the nanoparticles. A sample perhaps on a microscope slide can be suspended within a magnetic field and may cause excitation of the particles perhaps even AC excitation to be induced to the nanoparticles or micro particles in the reagent. A magnetic field may include but is not limited to an AC field, a DC field, a permanent magnet, a series of electromagnets, an electromagnetic field, any combination thereof, and the like and may be generated by a field generator (30). A field generator (30) may be a series of generators which may create multiple magnetic fields near a sample and may even be a variable strength magnetic field generator which may provide varying strengths of a magnetic field. A field generator (30) may be located near a sample and a liquid perhaps above a sample, below a sample support element, both above and below a sample as understood from FIG. 17, on the side of a sample and the like. In embodiments, a wand (4) may be a conducting wand. For example, a conducting AC field or even an AC excitation may result in random movements of the particles suspended in liquid and may create thermal agitation of the molecules that may compose the surrounding liquid. The random motion may be defined as Brownian motion.

Figure 17:
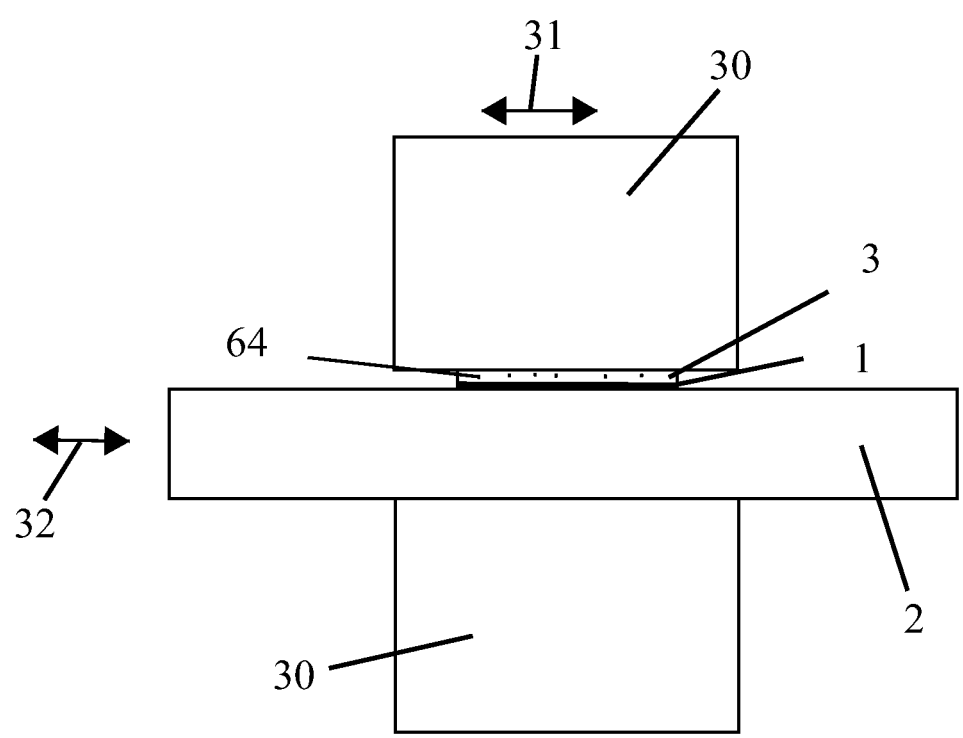
FIG. 17 shows a conceptual example of an electric field or a magnetic field applied to a liquid in accordance with some embodiments of the present invention.

In embodiments a sample (1) with a liquid perhaps having at least some nanoparticles (64) therein may be placed within a magnetic field (21). A field may be moved with respect to a sample and reagent by perhaps moving the magnetic field generator (31) or by moving a sample perhaps with a sample support element (32) as shown in FIG. 17.

If the slide may be moved under a magnetic field or the magnetic field may be moved over the slide, in addition to the Brownian motion, there can be an increase in the kinetic energy of the system thereby significantly reducing the time required to stain a sample and reduce the amount of reagents and antibodies required in the process. A conventional protocol which may take a minimum of about 1 hour can be completed as rapidly as between about 15 and about 30 minutes or perhaps even less then about 30 minutes. Therefore, an activity enhancer of a reagent may provide fast staining of a sample. The effect may be velocity dependant. A conducting AC field may generate heat, and the combination of heat and random movements of nanoparticles may aid in better staining by reducing time to complete the staining process and may increase the kinetics. The effect may be the same without nanoparticles by a conducting AC field and creating Brownian motion of antibodies and surrounding molecules.

Exposing the sample carrier (e.g., microscope slide with tissue) perhaps with or without movement to AC or DC or permanent magnet field may improve the staining. The combination of nanoparticle conjugated reagents and a conducting AC or DC or permanent magnetic field may improve staining and may helps with the quantification of cancerous cells.

The AC, DC, or perhaps even permanent magnets methods may utilize a device which may create magnetic fields through samples mounted on microscope slides with reagent and perhaps even antibody solutions which may or may not contain nanoparticles or micro particles. The resulting AC excitation may be created by a series of electromagnets which may 1) increase the electrostatic charge of the reagents or may 2) move the reagent over the slide in a line. A device, perhaps defined by the pole piece width and the aliquot size, may affect the sample through multiple magnetic fields energized sequentially along the length of the slide. Reagents with the nanoparticles may move across a sample perhaps as the units may be excited serially back and forth which may also induce kinetic energy at the trailing edge of the reagent meniscus or alternatively may increase the electrostatic charge of the reagents. A moving magnetic field (31) may provide attraction between nanoparticles and the magnetic field and may provide that a reagent may move in line with a moving magnetic field. This mechanism may also be used to wash the tissue with a buffer wash by serially flow of a moving buffer wash. The same results may be obtained by a variation of this system where a slide could be moved within a single magnetic field. An alternative to electromagnetic fields used in these devices could be the use of permanent magnets to create the magnetic field.

In embodiments of the present invention, methods may be provided to increase the electrostatic charge of the reagents perhaps reducing the reaction time and even improving the quality of tissue staining. Magnetic field lines may be held constant per unit area. Chemistry may be inserted within a cross section area of this field. Then, a transverse motion may be created between reagent and magnetic field lines which may increase the electric field lines in the chemistry per unit area. The magnetic field may be changed in amplitude and/or polarity perhaps while holding the electrostatic field lines stationary in the reagent. This may increase the electric field line per unit area in the reagent. A solution with nanoparticles may be provided at a concentration level and nanoparticle size which may not affect the staining process. When subjected to a changing magnetic field, additional electric field lines may be formed in the reagent perhaps by the reversal of the magnetic poles of the particles. A DC magnetic field may be used with physical motion perhaps by the pole piece or even the slide, and the degree of electric field may be a function of the velocity of the relative motion of the pole piece and slide. Conducting DC magnetic fields may move the reagent with nanoparticles by capillary action across the slide perhaps creating agitation resulting in increased kinetic energy. Conducting DC fields may generate heat and combination of heat and random movements of nanoparticles may aid in staining in less time by perhaps increasing the kinetics. The effect may be the same without nanoparticles by a conducting DC field and by creating Brownian motion of antibodies and surrounding molecules. When using magnetic field lines to pull a wash buffer across a slide by attracting nanoparticles, the trailing edge of the wash buffer meniscus may electrostatically attract impurities on the slides and may clean the slide. It may be desirable to utilize various or even all forms of changing magnetic fields either by physical movement or perhaps by electronically changing field line strengths for the purpose of increasing reagent electrical charge. It may be desirable to utilize audio and perhaps even an ultrasonic transducer to supply the transverse motion as well as perhaps the use of white noise or any other periodic waves as a signal source for a modulation source. It may be desirable to increase the electrostatic force perhaps by increasing the number of field lines in the molecular structure of the reagent by moving transverse magnetic field lines through it which may increase electrostatic attraction. It may also be desirable to increase the number of electrostatic field lines in the chemistry of the reagent perhaps by changing the amplitude and polarity of the traverse magnetic field.

The present invention may provide embodiments of a sample processing system comprising a plurality of slides used for the handling and processing of samples and sample support elements such as slides or microscope slides where each sample may be treated with different processing protocols. Other sample carriers may be accommodated consistent with the present invention. Each slide carrier or holder or tray may be configured to accommodate sample carrier retainment assemblies, such as slide retainment assemblies, carrier racks, modules, or magazines. The slide retainment assembly may comprise a slide rack, module, or magazine. A slide retainment assembly may be configured to accommodate a plurality of slides.

One or more drawers or carousals or trays may be provided to accommodate processing materials such as reagent containers for sample processing. A processing material retainment assembly, such as a container rack may be utilized to accommodate reagent containers or other processing materials within each of the drawers. Bottle inserts may be preferably configured with the retainment assembly to ensure proper processing material positioning within the processing material retainment assembly and the drawer or tray or carrier.

Embodiments of the present invention may further comprise an arm utilized in sample processing, potentially having robotic movement, and in some embodiments, Cartesian movement. The arm may comprise one or more elements, such as an actuator probe such as a syringe, a sensor element, an optical sensor (including but not limited to a camera or a CCD device), and even a non-discrete volume fluid and/or air applicator. The optical sensor may even be configured to sense temperature such as through IR detection or the like. A reagent container perhaps with bird feeder concept may be utilized by touching or even pushing a lever to dispense between about 100 and about 150 micro liters of reagent on a slide or perhaps even up to about 1000 micro liters per reagent step.

Important for many immunohistochemistry applications and many other sample processing sequences and protocols are temperature characteristics associated with a sample, sample carrier, and the processing environment. Accordingly, the present invention may comprise an automated sample processing system comprising a temperature regulation system or a temperature regulation device and a sample processing control system to which the temperature regulation system may be responsive with perhaps active temperature regulation (e.g., temperature control with both heating and cooling) and even within certain tolerances. It may also be adaptive as mentioned above for antigen retrieval and maintaining temperature between about 2 to about 8 degrees C., for unstable reagents. Staining process will be processed at about 24° C., and perhaps ±about 2° C. or ±about 1° C.

Configurations of the temperature regulation system may include a Peltier device or Peltier temperature control, and in configurations such as a heat sink or fan in the inside chamber to control the temperature. The other heat sink or fan of the pair may be on the outside of the controlled volume, where it may be exposed to the ambient environment of the laboratory. One or more thermoelectric devices perhaps including the electrical junctions themselves may be located on the boundary between the interior and exterior. The TED or TEDs may generate a hot portion and a cold portion and may aid in moving heat into or out of the desired location. The "hot" portion may be configured to distribute heat from the exterior of the controlled interior volume. If the temperature of the "hot" portion of the TED is controlled to maintain a low temperature, such as with a controlled paired heat sink/fan, the corresponding "cold" portion of the TED, may be configured within the controlled interior volume, may be colder by a corresponding amount, and may act in conjunction with a paired heat sink/fan as a controlled refrigerator, and may even actively reduce the temperature of the interior volume, or may achieve protocol tolerances as further described below. Such an item may serve as a temperature reduction element for various locations or purposes as described below.

As mentioned above, the internal temperature of the system may be controlled by an adaptive sample processing control system. Some applications may provide temperatures at about 24° C.±about 2° C.; in other embodiments the internal ambient temperature may be maintained at about 24° C. comprises ±an incremental range, such as a non-integer incremental range. One temperature regulation system of the present invention may comprise one or more heat pumps, and in some embodiment of the present invention's two thermoelectric heat pumps. The temperature regulation system may feature each heat pump module having a heat sink and fan on either side of the TED.

Embodiments of the invention may include regulating temperature in the antigen retrieval process; actively regulating temperature and even reducing temperature; controlling reduction of temperature; ramping temperature up or down; determining a processing sequence for it, determining at least one temperature tolerance, actively regulating temperature corresponding to the tolerance, or the like. All the above temperature control process may be applicable to the antigen retrieval and/or deparaffinization process in an automated stainer in various embodiments of the present invention. The various embodiments of the disclosed temperature regulation system may feature the capability of controlling reagent temperature alone or in addition to an antigen retrieval temperature. One embodiment of a reagent temperature regulation system may include a conduction temperature regulation system. A reagent temperature regulation system may have conductive regulation elements perhaps mounted below the reagent tray. The conductive regulation elements may feature thermoelectric regulation features such as Peltier-type temperature regulation. Naturally, a sensing element may be provided as part of a sample processing configuration and may be incorporated to sense temperature, perhaps even instantaneously. This may assist in maintaining temperature tolerances and in controlling rates of temperature change. Photodiode devices, electric conductivity devices, IR sensors, sensors acting through septa of a container, or other sensors may be included to sense values such as reagent containers or slides collectively or individually.

As previously mentioned, reagents may play a vital role in the staining sequence of many processing protocols. The quality of the reagents, therefore, may be important for adequate sample processing. In order to maintain shelf life of the reagents of the sample processing system, the reagent temperatures may also be controlled such as by a reagent temperature control element to maintain desirable temperatures, especially respective of typical ambient temperatures of the processing system and temperature effects from outside environments such as typical laboratories environments that may lack appropriate temperature control for the processing system. This may include maintaining the reagent at a temperature specified by the manufacturer, such as between about 2 and about 8 degrees C., so that the manufacturer shelf life is fully maintained and not shortened. The temperature control for maintaining reagent shelf life may apply for unstable reagents at room temperature and can be controlled with in a range of about 2 and about 8 degrees C., by using an isolated cold spot controlled by Peltier device.

The reagent may be identified by reading the label with an identification system or perhaps even a combination of identification systems. The identification system reader in combination with software scheduler may determine which reagent needs to be dispensed for a particular slide. Application and usage of identification systems in embodiments of the present invention perhaps to identify slides and reagents may include but are not limited to: barcode in perhaps 1D or even 2D matrix, RFID, smart card, I button, mini button IR, OCR, either alone or perhaps in combination, as well as other identifications systems. Stainer software can be capable of integrating the PPID and LIS systems. A microscope slide could be marked with laser etching, direct marking, laser printing, or the like.

The slide sample to be stained may be identified by reading the label with an identification system or perhaps even a combination of identification systems. An identification system reader may determine a set of reagents needed for a particular slide. The protocols processed on one slide or even on a plurality of slide can be common or different protocols. Processing of protocols may involve application of different reagents to different slides with perhaps even different incubation times. The length of the protocol steps/sequence may be same or different in a group of slides processed.

It may be desirable to provide adequate control of processing characteristics such as temperature, pH, concentration of antibody, relative humidity, buffer constituents, salts added and dilution used. Control of the processing samples may be accomplished with a sample processing system manager such as a computer server connected with one or more sample processing systems. Connection among perhaps a number of process systems and perhaps a number of computers, such as workstations and a server (the latter residing either separately or as part of a workstation), may be achieved by use of a local area network (LAN), such as a group of computers and associated devices that share a common communications line or perhaps wireless link and may even share the resources of a single processor, memory, or server within a small geographic area (for example, within an office building or complex). Connection may also be established to a laboratory network, facilities intranet system, or even a laboratory information system such as through a bridge. Temperature values, historical actions, and particular timing activities may be captured and stored for local or remote access through the use of such a system.

As can be easily understood from the foregoing, the basic concepts of the present invention may be embodied in a variety of ways. It involves both staining techniques as well as devices to accomplish the appropriate stainer. In this application, the staining techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims that will be included in any subsequent patent application.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. It should be understood that such language changes and broader or more detailed claiming may be accomplished at a later date (such as by any required deadline) or in the event the applicant subsequently seeks a patent filing based on this filing. With this understanding, the reader should be aware that this disclosure is to be understood to support any subsequently filed patent application that may seek examination of as broad a base of claims as deemed within the applicant's right and may be designed to yield a patent covering numerous aspects of the invention both independently and as an overall system.

Further, each of the various elements of the invention and claims may also be achieved in a variety of manners. Additionally, when used or implied, an element is to be understood as encompassing individual as well as plural structures that may or may not be physically connected. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "stainer" should be understood to encompass disclosure of the act of "staining"—whether explicitly discussed or not—and, conversely, were there effectively disclosure of the act of "staining", such a disclosure should be understood to encompass disclosure of a "stainer" and even a "means for staining." Such changes and alternative terms are to be understood to be explicitly included in the description.

Any patents, publications, or other references mentioned in this application for patent are hereby incorporated by reference. Any priority case(s) claimed by this application is hereby appended and hereby incorporated by reference. In addition, as to each term used it should be understood that unless its utilization in this application is inconsistent with a broadly supporting interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in this patent application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s).

Thus, the applicant(s) should be understood to have support to claim and make a statement of invention to at least: i) each of the stainer devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, xii) each potentially dependent claim or concept as a dependency on each and every one of the independent claims or concepts presented, and xiii) all inventions described herein.

In addition and as to computer aspects and each aspect amenable to programming or other electronic automation, the applicant(s) should be understood to have support to claim and make a statement of invention to at least: xvi) processes performed with the aid of or on a computer as described throughout the above discussion, xv) a programmable apparatus as described throughout the above discussion, xvi) a computer readable memory encoded with data to direct a computer comprising means or elements which function as described throughout the above discussion, xvii) a computer configured as herein disclosed and described, xviii) individual or combined subroutines and programs as herein disclosed and described, xix) the related methods disclosed and described, xx) similar, equivalent, and even implicit variations of each of these systems and methods, xxi) those alternative designs which accomplish each of the functions shown as are disclosed and described, xxii) those alternative designs and methods which accomplish each of the functions shown as are implicit to accomplish that which is disclosed and described, xxiii) each feature, component, and step shown as separate and independent inventions, and xxiv) the various combinations and permutations of each of the above.

With regard to claims whether now or later presented for examination, it should be understood that for practical reasons and so as to avoid great expansion of the examination burden, the applicant may at any time present only initial claims or perhaps only initial claims with only initial dependencies. The office and any third persons interested in potential scope of this or subsequent applications should understand that broader claims may be presented at a later date in this case, in a case claiming the benefit of this case, or in any continuation in spite of any preliminary amendments, other amendments, claim language, or arguments presented, thus throughout the pendency of any case there is no intention to disclaim or surrender any potential subject matter. It should be understood that if or when broader claims are presented, such may require that any relevant prior art that may have been considered at any prior time may need to be re-visited since it is possible that to the extent any amendments, claim language, or arguments presented in this or any subsequent application are considered as made to avoid such prior art, such reasons may be eliminated by later presented claims or the like. Both the examiner and any person otherwise interested in existing or later potential coverage, or considering if there has at any time been any possibility of an indication of disclaimer or surrender of potential coverage, should be aware that no such surrender or disclaimer is ever intended or ever exists in this or any subsequent application. Limitations such as arose in *Hakim v. Cannon Avent Group, PLC,* 479 F.3d 1313 (Fed. Cir 2007), or the like are expressly not intended in this or any subsequent related matter. In addition, support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant has intended to capture as full and broad a scope of coverage as legally available. To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible. The use of the phrase, "or any other claim" is used to provide support for any claim to be dependent on any other claim, such as another dependent claim, another independent claim, a previously listed claim, a subsequently listed claim, and the like. As one clarifying example, if a claim were dependent "on claim 20 or any other claim" or the like, it could be re-drafted as dependent on claim 1, claim 15, or even claim 25 (if such were to exist) if desired and still fall with the disclosure. It should be understood that this phrase also provides support for any combination of elements in the claims and even incorporates any desired proper antecedent basis for certain claim combinations such as with combinations of method, apparatus, process, and the like claims.

Finally, any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A method for efficient processing of a non-liquid biological sample with a dynamically moving aqueous-based processing liquid, comprising the steps of:
   providing a stationary sample support with a hydrophilic surface;
   providing the non-liquid biological sample fixed on the stationary sample support;
   providing a moveable wand positioned above the sample support element, the movable wand having a substantially flat hydrophobic surface;
   applying the aqueous-based processing liquid to the stationary sample support with the non-liquid biological sample;
   contacting said substantially flat hydrophobic surface of the moveable wand with the aqueous-based processing liquid;
   forming a substantially contained liquid bridge with the aqueous-based processing liquid between the substantially flat hydrophobic surface of the wand and the hydrophilic surface of the stationary sample support;
   steadily oscillating the moveable wand back and forth above the stationary sample support and the non-liquid biological sample, therefore steadily oscillating the substantially contained liquid bridge over the stationary sample support and the non-liquid biological sample; and efficiently processing the non-liquid biological sample with the aqueous-based processing liquid.

2. The method according to claim 1 wherein the step of steadily oscillating the moveable wand back and forth is performed with a constant velocity.

3. The method according to claim 1 wherein the step of steadily oscillating the moveable wand back and forth is performed with a variably velocity.

4. The method according to claim 1 wherein the substantially contained liquid bridge comprises a meniscus at each of its sides.

5. The method according to claim 1 further comprising compressing the oscillating liquid bridge between the wand and the sample support thus forming sliding reagent friction between the oscillating liquid bridge and the non-liquid biological sample.

6. The method according to claim 1 wherein the non-liquid biological sample is selected from a group consisting of a untreated tissue, pretreated tissue, antigen retrieved tissue, epitope retrieved tissue, deparaffinized tissue, histological sample, cell specimens, cell lines, cell membrane, cell preparations, proteins, synthetic peptides, bodily fluids, bone marrow, cytology specimens, blood smears, and any combination thereof.

7. The method according to claim 1 wherein the stationary sample support comprises a glass slide.

8. The method according to claim 1 wherein the step of steadily oscillating the moveable wand back and forth comprises providing that each movement of the substantially contained liquid bridge covers all of the non-liquid biological sample.

9. The method according to claim 1 wherein the step of efficiently processing the non-liquid biological sample comprises the step of staining said sample.

10. The method according to claim 9 wherein the step of staining the non-liquid biological sample provides a stained sample having a property selected from a group consisting of a sharp stain, crisp stain, a stained sample with substantially no background, a stained sample with substantially no non-specific staining, and a stained sample with substantially no hue on the sample support element.

11. The method according to claim 1, wherein forming a substantially contained liquid bridge with the aqueous-based processing liquid between the substantially flat hydrophobic surface of the wand and the hydrophilic surface of the stationary sample support comprises forming an acute angle between the liquid bridge and the hydrophilic surface of the stationary sample support and an obtuse angle between the liquid bridge and the hydrophobic surface of the wand.

12. The method according to claim 1 wherein the substantially flat hydrophobic surface comprises a rough hydrophobic surface.

13. The method according to claim 1 wherein the aqueous-based processing liquid comprises a reagent.

14. The method according to claim 13 wherein the reagent is selected from a group consisting of an unstable reagent, a stable reagent, a immunohistochemistry reagent, an in situ hybridization reagent, a histochemical reagent, a pretreatment reagent, a reagent for deparaffinization, a reagent for antigen retrieval, and any combination thereof.

15. The method according to claim 13 wherein the reagent comprises at least one component selected from a group consisting of antibodies, probes, antibody-enzyme conjugates, enzymes, nanoparticles, and any combination thereof.

16. The method according to claim 1 wherein the aqueous-based processing liquid comprises a buffer.

17. The method according to claim 16 wherein the buffer comprises a wash buffer.

18. The method according to claim 1 wherein the aqueous-based processing liquid comprises a stain.

19. The method according to claim 18 wherein the stain comprises at least one component selected from a group consisting of chromogenic substrates, chromogenic activator, chromogens, counterstains, and any combination thereof.

* * * * *